United States Patent
Bromage et al.

(10) Patent No.: US 10,734,209 B2
(45) Date of Patent: Aug. 4, 2020

(54) REAGENTS AND METHODS FOR SIMULTANEOUSLY DETECTING ABSOLUTE CONCENTRATIONS OF A PLURALITY OF ELEMENTS IN A LIQUID SAMPLE

(71) Applicant: New York University, New York, NY (US)

(72) Inventors: Timothy G. Bromage, New York, NY (US); Melanie Bäuchle, New York, NY (US)

(73) Assignee: New York University, New York, NY (US)

( * ) Notice: Subject to any disclaimer, the term of this patent is extended or adjusted under 35 U.S.C. 154(b) by 471 days.

(21) Appl. No.: 15/728,485

(22) Filed: Oct. 9, 2017

(65) Prior Publication Data

US 2018/0102240 A1    Apr. 12, 2018

Related U.S. Application Data

(60) Provisional application No. 62/405,830, filed on Oct. 7, 2016.

(51) Int. Cl.
*H01J 49/00* (2006.01)
*G01N 33/18* (2006.01)
*H01J 49/10* (2006.01)

(52) U.S. Cl.
CPC ........ *H01J 49/0009* (2013.01); *G01N 33/182* (2013.01); *G01N 33/1813* (2013.01); *H01J 49/105* (2013.01)

(58) Field of Classification Search
USPC ........................................... 250/251
See application file for complete search history.

(56) References Cited

U.S. PATENT DOCUMENTS

| | | | |
|---|---|---|---|
| 9,330,892 B2 | 5/2016 | Ardelt et al. | |
| 2006/0239882 A1* | 10/2006 | Seo | C01G 55/00 423/263 |
| 2011/0155903 A1 | 6/2011 | Ardelt et al. | |

OTHER PUBLICATIONS

Ding et al., "Inductively Coupled Plasma Mass Spectrometry for the Simultaneous Determination of Thirty Metals and Metalloids Elements in Blood Samples," Chin. J. Prey. Med., 46:745-749 (2012) English Abstract Only.

Heitland et al., "Biomonitoring of 37 Trace Elements in Blood Samples From Inhabitants of Northern Germany by ICP-MS," Journal of Trace Elements in Medicine and Biology, 20:253-262 (2006).

Goulle et al., "Metal and Metalloid Multi-Elementary IPC-MS Validation in Whole Blood, Plasma, Urine and Hair Reference Values," Forensic Science International 153:39-44 (2005).

(Continued)

*Primary Examiner* — Kiet T Nguyen
(74) *Attorney, Agent, or Firm* — Pepper Hamilton LLP

(57) ABSTRACT

Disclosed herein are internal standard compositions, a plurality of calibration standards, and one or more kits for use with mass spectrometry, particularly for use with an inductively coupled plasma mass spectrometer capable of simultaneous detection of a large number of ionization products over a large range of masses. Methods of using these reagent materials for the simultaneously detection of absolute concentrations of a plurality of elements in a liquid sample.

23 Claims, 3 Drawing Sheets
(3 of 3 Drawing Sheet(s) Filed in Color)

(56) References Cited

OTHER PUBLICATIONS

Zhang et al., "Developments in Determination of Elements Using ICP-MS in Blood and Urine," Fa Yi Xue Za Zhi, 28 (6)456-460 (2012) English Abstract Only.

Rahil-Khazen et al., "Validation of Inductively Coupled Plasma Atomic Emission Spectrometry Technique (ICP-AES) for Multi-Element Analysis of Trace Elements in Human Serum," Scand. J. Clin. Lab Invest 60(8):677-686 (2000).

Liu et al., "Simultaneous Determination of 12 Trace Elements in Children Plasma Sample by High Resolution Inductively Coupled Plasma Mass Spectrometry," Wei Sheng Yan Jiu. 43(2):296-300 (2014) English Abstract Only.

D'ilio et al., "Simultaneous Quantification of 17 Trace Elements in Blood by Dynamic Reaction Cell Inductively Coupled Plasma Mass Spectrometry (DRC-ICP-MS) Equipped With a High-Efficiency Sample Introduction System," Anal. Chim. Acta. 579(2):202-208 (2006).

Fernandez-Turiel et al., "Strategy for Water Analysis Using ICP-MS," Fresenius J. Anal. Chem. 368(6):601-606 (2000).

Gonzalvez et al., "Searching the Most Appropriate Sample Pretreatment for the Elemental Analysis of Wines by Inductively Coupled Plasma-Based Techniques," J. Agric. Food Chem. 56(13):4943-4954 (2008).

Forrer et al., "Simultaneous Measurement of the Trace Elements Al, As, B, Be, Cd, Co, Cu, Fe, Li, Mn, Mo, Ni, Rb, Se, Sr, and Zn in Human Serum and Their Reference Ranges by ICP-MS," Biol. Trace Elem. Res. 80(1):77-93 (2001).

Taylor et al., "Multielement Analysis of Canadian Wines by Inductively Coupled Plasma Mass Spectrometry (ICP-MS) and Multivariate Statistics," J. Agric. Food Chem. 51(4):856-860 (2003).

"A New Era in ICP Mass Spectrometry: Spectro MS Simultaneously Records the Contents of More Than 75 Elements With Approx. 210 Isotopes," Spectro Ametek Press Release, Mar. 1, 2010.

Morton et al., "Determination of 61 Elements in Urine Samples Collected From a Non-Occupationally Exposed US Adult Population," Toxicology Letters 231:179-193 (2014).

White et al., "Trace Element Reference Values in Tissues From Inhabitants of the European Union. X. A Study of 13 Elements in Blood and Urine of a United Kingdom Population," The Science of the Total Environment 216:253-270 (1998).

Monaci et al., "Concentrations of Major Elements and Mercury in Unstimulated Human Saliva," Biological Trace Element Research 89:193-203 (2002).

Selih et al., "Multi-Element Analysis of Wines by ICP-MS and ICP-OES and Their Classification According to Geographical Origin in Slovenia," Food Chemistry 153:414-423 (2014).

Coetzee et al., "Intrareginal Classification of Wine via ICP-MS Elemental Fingerprinting," Food Chemistry 164:485-492 (2014).

Kment et al., "Differentiation of Czech Wines Using Multielement Composition—A Comparison With Vineyard Soil," Food Chemistry 91:157-165 (2005).

Minoia et al., "Trace Element Reference Values in Tissues From Inhabitants of the European Community I. A Study of 46 Elements in Urine, Blood and Serum of Italian Subjects," The Science of the Total Environment 95:89-105 (1990).

Cornelis et al., "Trace Element Reference Values in Tissues From Inhabitants of the European Community. VII. Review of Trace Elements in Blood, Serum and Urine of the Belgian Population and Critical Evaluation of Their Possible Use as Reference Values," The Science of the Total Environment 158:191-226 (1994).

Iyengar et al., "Trace Elements in Human Clinical Specimens: Evaluation of Literature Data to Identify Reference Values," Clinical Chemistry 34(3):474-481 (1988).

Fernandes et al., "Wine Fingerprinting Using a Bio-Geochemical Approach," BIO Web of Conferences 5:02021-o.1-02021-p. 4 (2015).

Kucera et al., "Review of Trace Elements in Blood, Serum and Urine for the Czech and Slovak Populations and Critical Evaluation of Their Possible use as Reference Values," The Science of the Total Environment 166:211-234 (1995).

* cited by examiner

REAGENTS AND METHODS FOR SIMULTANEOUSLY DETECTING ABSOLUTE CONCENTRATIONS OF A PLURALITY OF ELEMENTS IN A LIQUID SAMPLE

This application claims the priority benefit of U.S. Provisional Patent Application Ser. No. 62/405,830, filed Oct. 7, 2016, which is hereby incorporated by reference in its entirety.

FIELD OF THE INVENTION

This invention relates generally to the development of reagents and methods for using those reagents according to a calibration method that allows for simultaneous measurement of elements $^6$Li to $^{238}$U via inductively coupled plasma mass spectrometry ("ICP-MS").

BACKGROUND OF THE INVENTION

Water is a molecule composed of two hydrogen atoms and one oxygen atom. Due to its unique physical and chemical properties, it has a tremendous ability to dissipate materials into their constituent molecules and elements, which makes pure water almost non-existent in nature. What generally is called water is actually an accumulation of dissolved elements in water. Elements in water can occur in their organic or inorganic form, and are mostly combined in molecules.

The elemental content of water typically mirrors its natural environmental exposure, e.g., its mineral content reflects the geochemical environment through which water runs (Henshaw et al., 1989; Fernandez-Turiel et al., 2000). Aqueous solutions employ water as a medium, and as such, in the case of, say, beverages, the elemental content will additionally include the effects of manufacturing processes. Aqueous biofluids primarily reflect biological functions and environmental exposure. Some aqueous solutions, such as commercial milk, will include elemental signature that reflect beverage manufacturing as well as those of biofluids. In all, aqueous solutions are expected to "fingerprint" their origin.

In theory, each naturally occurring element can be dissolved in water, and each element of the complete inorganic mass range from $^6$Li to $^{238}$U can be found in water, but in practice there is no comprehensive method for measuring their concentrations.

There are several techniques and methods to detect and quantify elements in fluids, and water in particular, such as high pressure liquid chromatography ("HPLC"), inductively coupled plasma atomic emission spectrometry ("IPC-AES"), inductively coupled plasma optical emission spectrometry ("ICP-OES"), and most prominently inductively coupled plasma mass spectrometry ("ICP-MS") (Kubová et al., 1994; Rahil-Khazen et al., 2000; Leonhard et al., 2002; Taylor et al., 2003; Gonzálvez et al., 2008; Krachler and Shotyk, 2009; Ding et al., 2012; Pröfrock and Prange, 2012; Khan et al., 2013; Loop et al., 2013; Yeghicheyan et al., 2013; Jabłońska-Czapla et al., 2014; and Šelih et al., 2014).

For almost three decades, ICP-MS has been used to detect and quantify elements in various fluid samples ranging from water to breast milk, wine and body fluids (Henshaw et al., 1989; Ding et al., 2012; Krachler and Shotyk, 2009; Ammann, 2002; Ardelt et al. 2013; D'Ilio et al., 2006; De Boer et al., 1996; Forrer et al, 2001; Goullé et al., 2005; Heitland et al., 2006; Kantipuly et al., 1988; Long et al., 1989; Lyon et al., 1988; Mohd-Taufek et al. 2016; Staff et al., 2014; Stetzenbach et al., 1994; Zhang et al., 2012). Hence, ICP-MS is the technique issued by national and international guidelines to monitor water quality (Krachler and Shotyk, 2009; Heitland et al., 2006; Long et al., 1989; Louie et al., 2012; and WHO, 2011).

Although each ICP-MS has the theoretical potential for detecting each element, investigators have not done so. Until recently, all ICP-MS instruments have been so-called "sequential" ICP-MS (se-ICP-MS), in which elements are analyzed consecutively, one by one. However, a constraint over the employ of se-ICP-MS is that sample volumes must be relatively high to dispense to the instrument whilst measuring one element after the other, and significant time and consumables are required to operate these instruments; this makes it impractical to evaluate the entire relevant inorganic spectrum with se-ICP-MS.

Nevertheless, for some years se-ICP-MS has been successfully used to determine abundances and concentrations of some multiple number of elements, mostly trace elements or rear earth elements (REE), in various water samples (Henshaw et al., 1989; Stezenbach et al., 1994; DeBoer et al., 1996; Leonhard et al., 2002; Krachler and Shotyk, 2009; Louie et al., 2012), wine (Taylor et al., 2003; Gonzálvez et al., 2008; Šelih et al., 2014; and Khan et al., 2014), milk and formula (Khan et al., 2013; Khan et al., 2014), saliva, blood and urine (Lyon et al., 1988; Forrer et al., 2001; Staff et al., 2014: Koh et al., 2003; Goullé et al., 2005; Barbosa et al., 2006; D'Ilio et al., 2006; Heitland and Köster, 2006; Nriagu et al., 2006; Ding et al., 2012; and Zhang et al., 2012), liquefied tomatoes (Bressy et al., 2013) as well as in sediments and rocks (Garbe-Schönberg, 1993; Loop et al., 2013). However, because of the aforementioned constraints, se-ICP-MS studies rarely exceed 30 elements.

Recently developed "simultaneous" ICP-MS (si-ICP-MS) permits multiple elements to be detected in one evaluation from small sample volumes in seconds and at relatively low consumables and personnel costs. In 2013, the SPECTRO SI-ICP-MS (SPECTRO Analytical Instruments GmbH, Kleve, Germany) was introduced (Ardelt et al., 1998) having 4,800 detector elements, which is large enough to simultaneously detect isotope signals over the full relevant inorganic mass spectrum from $^6$Li to $^{238}$U (technical specifications can be found in Ardelt et al., 2013). With this technology it is possible to quantify the relatively complete elemental composition of an aqueous sample with as little as 1 mL per fluid sample. However, while the technology is able, no method has to date been developed to evaluate the complete spectrum simultaneously. An si-ICP-MS calibration method is needed for the simultaneous measurement from $^6$Li to $^{238}$U.

The urgent need for such a comprehensive method, especially for water, is justified by the lack of even basic data regarding element abundances and concentrations for most elements across the breadth of the inorganic spectrum (Fernandez-Turiel et al., 2000; Heitland and Köster, 2006; PAPERS describing this lack). For example, the European Union (EU) and the United States Environmental Protection Agency (EPA) are monitoring and have issued maximum concentration limits for a number of elements in drinking water considered to be health risks (EU Directive, C., 1998; EU Regulations; US EPA, 2012), yet many elements commonly known as harmful to human health, such as lithium or tin, are neither monitored nor regulated in drinking water.

The present invention is directed to overcoming these and other deficiencies in the art.

SUMMARY OF THE DISCLOSURE

A first aspect of the invention relates to an internal standard composition for mass spectrometry, particularly for use with an inductively coupled plasma mass spectrometer capable of simultaneous detection of a large number of ionization products over a large range of masses. The internal standard composition according to this aspect comprises a combination of three elements selected from different periods on the periodic table of elements, wherein each of the three elements is present at a concentration within a range of about 0.05 to about 100 mg/L.

A second aspect of the invention relates to a blank standard composition for mass spectrometry, particularly for use with an inductively coupled plasma mass spectrometer capable of simultaneous detection of a large number of ionization products over a large range of masses. The blank standard includes ultrapure water, $HNO_3$, and an internal standard composition according to a first aspect of the invention.

A third aspect of the invention relates to a kit that that includes: an internal standard containing a combination of three elements selected from different periods on the periodic table of elements, the three selected elements being present in the internal standard at known concentrations; and a plurality of calibration standards, the plurality of calibration standards collectively comprising known concentrations of two or more of Li, Be, B, Na, Mg, Al, Si, P, S, Cl, K, Ca, Sc, Ti, V, Cr, Mn, Fe, Co, Ni, Cu, Zn, Ga, Ge, As, Se, Br, Rb, Sr, Y, Zr, Nb, Mo, Ru, Rh, Pd, Ag, Cd, In, Sn, Sb, Te, I, Cs, Ba, La, Ce, Pr, Nd, Sm, Eu, Gd, Tb, Dy, Ho, Er, Tm, Yb, Lu, Hf, Ta, W, Re, Os, Ir, Pt, Au, Hg, Tl, Pb, Bi, Th, and U (and preferably each of the recited elements), each of the calibration standards being provided in at least two different concentrations.

According to one embodiment, the internal standard is an internal standard according to the first aspect of the invention.

According to one embodiment, the plurality of calibration standards collectively comprise known concentrations of at least twenty of Li, Be, B, Na, Mg, Al, Si, P, S, Cl, K, Ca, Sc, Ti, V, Cr, Mn, Fe, Co, Ni, Cu, Zn, Ga, Ge, As, Se, Br, Rb, Sr, Y, Zr, Nb, Mo, Ru, Rh, Pd, Ag, Cd, In, Sn, Sb, Te, I, Cs, Ba, La, Ce, Pr, Nd, Sm, Eu, Gd, Tb, Dy, Ho, Er, Tm, Yb, Lu, Hf, Ta, W, Re, Os, Ir, Pt, Au, Hg, Tl, Pb, Bi, Th, and U; known concentrations of at least twenty-five of the recited elements from Li to U; known concentrations of at least thirty of the recited elements from Li to U; known concentrations of at least thirty-five of the recited elements from Li to U; known concentrations of at least forty of the recited elements from Li to U; known concentrations of at least forty-five of the recited elements from Li to U; known concentrations of at least fifty of the recited elements from Li to U; known concentrations of at least fifty-five of the recited elements from Li to U; known concentrations of at least sixty of the recited elements from Li to U; known concentrations of at least sixty-five of the recited elements from Li to U; known concentrations of at least seventy of the recited elements from Li to U; or known concentrations of each of the recited elements from Li to U.

According to another embodiment, the plurality of calibration standards include at least three different calibration standards, at least four different calibration standards, at least five different calibration standards, at least six different calibration standards, at least seven different calibration standards, at least eight different calibration standards, at least nine different calibration standards, or at least ten different calibration standards. In general, the fewest number of calibration standards should be used where that number of calibration standards does not cause interference, problems with element stability, or a conflation of too many isotopes, which can interfere with accurate measurements of individual elements.

A fourth aspect of the invention relates to a method for simultaneously detecting absolute concentrations of a plurality of elements in a liquid sample. This method comprises:

a) providing an internal standard comprising a combination of three elements selected from different periods on the periodic table of elements, the three selected elements being present in the internal standard at known concentrations;

b) providing a plurality of calibration standards, the plurality of calibration standards collectively comprising known concentrations of two or more of Li, Be, B, Na, Mg, Al, Si, P, S, Cl, K, Ca, Sc, Ti, V, Cr, Mn, Fe, Co, Ni, Cu, Zn, Ga, Ge, As, Se, Br, Rb, Sr, Y, Zr, Nb, Mo, Ru, Rh, Pd, Ag, Cd, In, Sn, Sb, Te, I, Cs, Ba, La, Ce, Pr, Nd, Sm, Eu, Gd, Tb, Dy, Ho, Er, Tm, Yb, Lu, Hf, Ta, W, Re, Os, Ir, Pt, Au, Hg, Tl, Pb, Bi, Th, and U (and preferably each of the recited elements), each of the calibration standards being provided in at least two different concentrations;

c) introducing a known concentration of the internal standard into each of the plurality of calibration standards, a blank standard, and a liquid sample to be tested; and d) introducing each of the plurality of calibration standards, the blank standard, and the liquid sample to be tested individually into an inductively coupled plasma mass spectrometer to simultaneously detect one or more ionization products of elements present in each of the plurality of calibration standards, the blank standard, and the liquid sample to be tested; and e) determining an absolute concentration of the one or more detected elements in the liquid sample relative to the one or more detected ionization products of elements in the plurality of calibration standards.

As used herein, the term "about" is used to define amounts, temperatures, pressures, times, pH values, percentages, and concentrations, and it will be appreciated that such variables are approximate and as such may vary by ±10%, for example ±5% and preferably ±2% (e.g. ±1%) from the numbers specified herein.

As noted above, while si-ICP-MS permits multiple elements to be detected in one evaluation from small sample volumes, lacking in the prior art was any description of a method for achieving simultaneous detection over the full relevant inorganic mass spectrum from $^{6}Li$ to $^{238}U$. Disclosed herein are reagents and a si-ICP-MS calibration method that allows for simultaneously detecting absolute concentrations of a plurality of elements, from $^{6}Li$ to $^{238}U$, in a liquid sample. Using these reagents and implementing the disclosed method, the present application demonstrates the simultaneous measurement of 71 elements from $^{6}Li$ to $^{238}U$ in aqueous samples, including water, beverages such as wine, beer, and milk, as well as biological samples such as saliva, urine, and blood plasma. Use of the invention described herein should be by spectroscopists knowledgeable in recognizing and correcting physical and spectral interferences in ICP-MS analysis

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
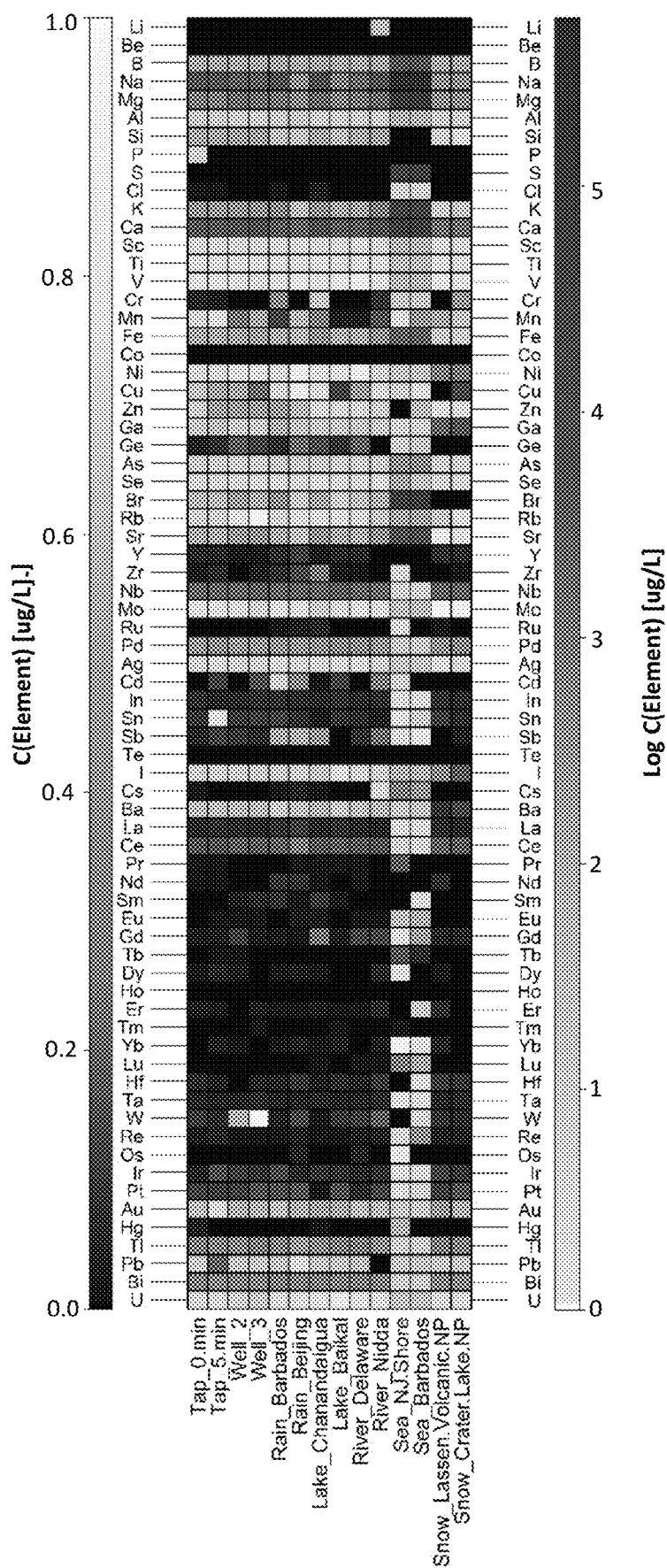
FIG. 1 shows the element concentration patters in environmental water. Trace concentrations between not detected (black) and 1 μg/L (white) are shown in shades of blue. Concentrations above 1 μg/L are represented by warm colors, in a logarithmic scale, and range from 1 μg/L (white) to over 800 mg/L (dark red).

Disclosed herein are reagents and methods for simultaneously detecting absolute concentrations of a plurality of elements, from $^6$Li to $^{238}$U, in a liquid sample.

The methods disclosed herein involve the use of an inductively coupled plasma mass spectrometer, preferably those containing a multichannel monolithic complementary metal oxide semiconductor (CMOS) strip detector array configured to simultaneously perform detection over a range of multiple masses, including from $^6$Li to $^{238}$U. One such si-ICP-MS device is available from SPECTRO Analytical Instruments GmbH (Kleve, Germany). The Spectro si-ICP-MS is described in U.S. Pat. No. 9,330,892 and "Spectro Recognized Among the Winners of R&D 100 Award," Spectro/Ametek Press Release, (Jul. 1, 2011), each of which is hereby incorporated by reference in its entirety. According to the above-noted press release, the Spectro/Ametek si-ICP-MS device is capable of achieving the simultaneous measurement over the full range of masses from $^6$Li to $^{238}$U due to the presence of (i) a novel ion optic that is extremely efficient in transporting ions from the plasma into the mass spectrometer while reliably removing neutral particles and photons from the beam; (ii) an electrostatic analyzer and a permanent magnet utilized to direct the ions onto a focal plane without additional scanning of the ion beam; (iii) a double focusing sector field mass spectrometer in Mattauch-Herzog geometry; (iv) an extremely powerful direct charge detector with 4,800 channels located in the focal plane of the mass spectrometer, which fully simultaneously records the entire mass spectrum from lithium to uranium from the continuous ion beam; and (v) each channel being divided into two separate detectors with different signal amplification, which enables the precise detection of even extreme isotope ratios.

The methods described herein involve the use of an internal standard that includes deionized ultrapure water (e.g. ≥18.2 MΩ) and a combination of three elements selected from different periods on the periodic table of elements, where the three selected elements are present in the internal standard at known concentrations. In certain embodiments, one of the three elements is selected from period 2, one of the three elements is selected from period 4 or period 5, and one of the three elements is selected from period 6 or period 7. In preferred embodiments, the internal standard does not contain more than four elements or even more than three elements, as this reduces the number of elements to be evaluated in various samples.

In certain embodiments, the three elements are each present in the internal standard at a concentration within a range of about 0.05 to about 100 mg/L, such as from about 0.1 to about 50 mg/L.

Internal standards are typically elements that are assumed not to occur in the test sample, or are assumed to be present in untraceable amounts, and therefore are not being calibrated; this is typically an element with only one isotope, or one very significant isotope. Furthermore, the internal standard should be in close proximity (in terms of their atomic number) to the measured, and calibrated, elements.

In various embodiments, the internal standard includes a known concentration of $^6$Li, a known concentration of $^{103}$Rh or $^{89}$Y, and a known concentration of $^{159}$Tb or $^{232}$Th. Rhodium, Yttrium, Terbium, and Thorium are single isotope elements and can be expected not to be present in most samples. Where one of these elements is expected in the test sample, then the alternative element should be used in the standard. Lithium, on the other hand, has two isotopes, Li$^6$ and Li', whose natural abundances are about 7.5% and about 92.5%, respectively. If lithium were to occur in a test sample, the concentration of Li$^6$ would be negligible. Therefore, using Li$^6$, Rh$^{103}$ or $^{89}$Y, and $^{159}$Tb or $^{232}$Th, the whole periodic table can be covered in terms of internal standards.

According to one embodiment, the three elements present in the internal standard composition are $^6$Li, Rh$^{103}$Rh, and $^{232}$Th. This standard can be used when detection of $^6$Li, $^{103}$Rh and $^{232}$Th in a test sample is not desired.

According to another embodiment, the three elements present in the internal standard, composition are $^6$Li, $^{103}$Rh, and $^{159}$Tb. This standard can be used when detection of $^6$Li, $^{103}$Rh and $^{159}$Tb in a test sample is not desired.

According to a further embodiment, the three elements present in the internal standard composition are $^6$Li, $^{89}$Y, and $^{232}$Th. This standard can be used when detection of $^6$Li, $^{89}$Y, and $^{232}$Th in a test sample is not desired.

According to yet another embodiment, the three elements present in the internal standard composition are $^6$Li, $^{89}$Y and $^{159}$Tb. This standard can be used when detection of $^6$Li, $^{89}$Y and $^{159}$Tb in a test sample is not desired.

In the various embodiments, $^6$Li is present in each internal standard at a concentration range of about 2 to about 50 mg/L, about 3 to about 40 mg/L, about 4 to about 30 mg/L, or about 5 to about 20 mg/L; one of $^{103}$Rh or $^{89}$Y is present in each internal standard at a concentration range of about 0.5 to about 50 mg/L, about 0.75 to about 40 mg/L, about 1 to about 30 mg/L, or about 1.25 to about 20 mg/L; and one of $^{159}$Tb and $^{232}$Th is present in each internal standard at a concentration range of about 0.5 to about 50 mg/L, about 0.75 to about 40 mg/L, about 1 to about 30 mg/L, or about 1.25 to about 20 mg/L.

Exemplary internal standard formulations comprise ultrapure water, $^6$Li at a concentration of about 10 mg/L, $^{89}$Y or $^{103}$Rh at a concentration of about 2 mg/L, and $^{159}$Tb or $^{232}$Th at a concentration of about 2 mg/L. Added to the internal standard is about 1% (v/v) ultrapure HNO$_3$.

The methods described herein involve the use of a plurality of calibration standards, which collectively comprise known concentrations of at least two of (and preferably each of) Li, Be, B, Na, Mg, Al, Si, P, S, Cl, K, Ca, Sc, Ti, V, Cr, Mn, Fe, Co, Ni, Cu, Zn, Ga, Ge, As, Se, Br, Rb, Sr, Y, Zr, Nb, Mo, Ru, Rh, Pd, Ag, Cd, In, Sn, Sb, Te, I, Cs, Ba, La, Ce, Pr, Nd, Sm, Eu, Gd, Tb, Dy, Ho, Er, Tm, Yb, Lu, Hf, Ta, W, Re, Os, Ir, Pt, Au, Hg, Tl, Pb, Bi, Th, and U. The concentration for each element is typically within the range of about 0.1 part per billion (ppb) to about 1000 parts per million (ppm), preferably from about 0.1 ppb to about 700 ppm. Each calibration standard contains ultrapure water, about 1% $HNO_3$ (to facilitate element release from sample tubes), the internal standard, and a known concentration of the selected element(s).

In certain embodiments, the plurality of calibration standards contain at least ten of the elements Li, Be, B, Na, Mg, Al, Si, P, S, Cl, K, Ca, Sc, Ti, V, Cr, Mn, Fe, Co, Ni, Cu, Zn, Ga, Ge, As, Se, Br, Rb, Sr, Y, Zr, Nb, Mo, Ru, Rh, Pd, Ag, Cd, In, Sn, Sb, Te, I, Cs, Ba, La, Ce, Pr, Nd, Sm, Eu, Gd, Tb, Dy, Ho, Er, Tm, Yb, Lu, Hf, Ta, W, Re, Os, Ir, Pt, Au, Hg, Tl, Pb, Bi, Th, and U, at least twenty of the recited elements, at least twenty-five of the recited elements, at least thirty of the recite elements, at least thirty-five of the recite elements, at least forty of the recited elements, at least forty-five of the recited elements, at least fifty of the recited elements, at least fifty-five of the recited elements, at least sixty of the recited elements, at least sixty-five of the recited elements, at least seventy of the recited elements, and preferably each of the recited elements.

Each of the calibration standards is preferably provided in at least two different concentrations, and in some embodiments at least three different concentrations. These standards should have a concentration range that covers the expected concentrations in samples analyzed.

The plurality of calibration standards are utilized, because the ICP-MS measures counts per second (cps) of elements on its detector, not actual concentrations of elements, which are not linearly related to cps. Molecules and elements are ionized by the high temperature of an argon plasma flame in the ICP-MS. The resulting ions are separated by their mass-to-charge ratio and counted on the device mass detector. The numbers of ions hitting the detector at a specific mass/charge ratio are recorded as counts per second. Calibration standards of determined concentrations of elements are read into (and stored into memory of) the ICP-MS, and the result correlated to cps. Hence, specific values of cps will be assigned to the calibration standard's respective concentration. A minimum of two (sometimes three) differently concentrated calibration standards and an additional blank standard are needed to produce a calibration regression formula, which is calculated by the processor associated with the ICP-MS and stored in memory. Using the calibration regression formula for each isotope, further measured counts per seconds (from samples) can be converted into concentrations of an element in a sample.

During the development of the present invention, it was discovered that inaccuracies are a direct result of one or more of the following: (i) a conflation of too many isotopes; (ii) so-called interferences; and (iii) stability. Increasing the amount of elements automatically increases the amount of isotopes, which leads to multiple isotopes with the same mass to charge ratio and therefore isotopes of multiple elements are measured together at one mass. Hence, the separating of isotope concentrations on the same mass is impossible. Interferences also may appear when ionized isotopes collide and fuse. This new molecule has the combined mass of both isotopes and is detected at its respective mass. For example, if the most common oxygen isotope $O^{16}$ fuses with the most common argon isotope $Ar^{40}$, the new molecule argon-oxide (ArO) has a mass of 56 and would be detected together with the most common iron isotope $Fe^{56}$. This makes it not possible to determine the correct amount of $Fe^{56}$. Potentially, each isotope of every element can collide with each isotope of every element, including itself. Therefore, reducing elements within one standard solution can reduce the risk of interferences and wrongly interpreted cps values. The possibility of isotopes fusing, of course, depends on their natural abundance and ionization energy: highly abundant isotopes such as $Mg^{24}$ are more likely to fuse than less abundant isotopes, such as $Mg^{25}$. Yet, although $Cl^{37}$ is less abundant than $Mg^{24}$, it has a much higher ionization energy and therefore is more likely to fuse. In addition, some elements destabilize in combination with other elements.

To ensure accurate measurements and avoid the problems described in the preceding paragraph, the plurality of calibration standards are selected and used iteratively to calibrate the ICP-MS instrument.

According to one embodiment, ten calibration standards are provided in two or three different concentrations. The ten standards are:

(i) a first calibration standard comprising Li, Be, B, Na, Mg, Al, K, Ca, V, Cr, Mn, Fe, Co, Ni, Cu, Zn, Ga, Ge, As, Se, Rb, Sr, Mo, Ag, Cd, Te, Ba, Tl, Pb, Bi, and U, typically at concentrations between about 5 ppb and about 50 ppm for each of the recited elements; and preferably at concentrations between about 10 to about 100 ppb for each of Ag, Al, Ba, Bi, Cd, Co, Cr, Cu, Ga, K, Li, Mg, Mo, Na, Ni, Pb, Rb, Sr, Tl, U, and V, between about 100 ppb to about 2 ppm for each of As, B, Be, Se, and Zn, and between about 1 ppm to about 10 ppm for Ca. One commercially available form for this standard is the Certipur® Certified Reference Material ICP multi-element standard VI available from Merck KGaA (Germany). These elements can be stored in about 5 to about 10% $HNO_3$.

(ii) a second calibration standard comprising Li, Be, B, Na, Mg, Al, K, Ca, V, Cr, Mn, Fe, Co, Ni, Cu, Zn, Ga, Ge, As, Se, Rb, Sr, Ag, Cd, Te, Ba, Tl, Pb, Bi, U, S, P, Si, In, and Cs, typically at concentrations between about 1 ppb and about 100 ppb for each of the recited elements; and preferably at concentrations between about 10 to about 50 ppb. One commercially available form for this standard is the Periodic Table Mix 1 for ICP, which is available from Sigma-Aldrich Co. LLC. The elements are stored in 10% $HNO_3$.

(iii) a third calibration standard comprising Ti, Ge, Zr, Nb, Mo, Ru, Rh, Pd, Sn, Sb, Hf, Ta, W, Re, Ir, Pt, and Au, typically at concentrations between about 1 ppb and about 100 ppb for each of the recited elements; and preferably at concentrations between about 10 to about 20 ppb. One commercially available form for this standard is the Periodic Table Mix 2 for ICP, which is available from Sigma-Aldrich Co. LLC. These elements are stored in 5% $HNO_3$ and 1% HF.

(iv) a fourth calibration standard comprising La, Ce, Pr, Nd, S, Eu, Gd, Tb, Dy, Ho, Er, Tm, Yb, Lu, Sc, and Y, typically at concentrations between about 1 ppb and about 100 ppb for each of the recited elements; and preferably at concentrations between about 10 to about 20 ppb. One commercially available form for this standard is the Periodic Table Mix 3 for ICP available from Sigma-Aldrich Co. LLC. These elements are stored in about 5% $HNO_3$.

(v) a fifth calibration standard comprising Os, typically at concentrations between about 1 and about 100 ppb, and preferably between about 10 to about 20 ppb. Os is stored in 10% v/v HCl.

(vi) a sixth calibration standard comprising Hg, typically at concentrations between about 0.1 and about 10 ppb, and preferably between about 1 to about 2 ppb. Hg is stored in 10% v/v $HNO_3$.

(vii) a seventh calibration standard comprising Cl, typically at concentrations between about 1 and about 1000 ppm, and preferably between about 150 to about 300 ppm. Cl is stored in water.

(viii) an eight calibration standard comprising Br, typically at concentrations between about 1 and about 100 ppb, and preferably between about 100 to about 200 ppb. Br is stored in water.

(ix) a ninth calibration standard comprising I, typically at concentrations between about 0.5 and about 50 ppb, and preferably between about 5 to about 10 ppb. I is stored in 1% TEA.

(x) a tenth calibration standard comprising Na, Mg, Ca, K, S, and P, typically at concentrations of between about 1 and about 500 ppm for each of Na, Mg, Ca, S, and P, and between about 0.1 and about 15 ppm for K; and preferably at concentrations between about 50 and about 150 ppm for each of Na and Mg, between about 100 and about 300 ppm for Ca, between about 20 and about 50 ppm for each of S and P, and between about 5 and about 8 ppm for K.

According to another embodiment, nine calibration standards are provided in two or three different concentrations. The nine standards are:

(i) a first calibration standard comprising Li, Be, B, Na, Mg, Al, K, Ca, V, Cr, Mn, Fe, Co, Ni, Cu, Zn, Ga, Ge, As, Se, Rb, Sr, Mo, Ag, Cd, Te, Ba, Tl, Pb, Bi, and U, typically at concentrations between about 5 ppb and about 50 ppm for each of the recited elements; and preferably at concentrations between about 10 to about 100 ppb for each of Ag, Al, Ba, Bi, Cd, Co, Cr, Cu, Ga, K, Li, Mg, Mo, Na, Ni, Pb, Rb, Sr, Tl, U, and V, between about 100 ppb to about 2 ppm for each of As, B, Be, Se, and Zn, and between about 1 ppm to about 10 ppm for Ca. One commercially available form for this standard is the Certipur® Certified Reference Material ICP multi-element standard VI available from Merck KGaA (Germany). These elements can be stored in about 5 to about 10% $HNO_3$.

(ii) a second calibration standard comprising Ti, Ge, Zr, Nb, Mo, Ru, Rh, Pd, Sn, Sb, Hf, Ta, W, Re, Ir, Pt, and Au, typically at concentrations between about 1 ppb and about 100 ppb for each of the recited elements; and preferably at concentrations between about 10 to about 20 ppb. One commercially available form for this standard is the Periodic Table Mix 2 for ICP, which is available from Sigma-Aldrich Co. LLC. These elements are stored in 5% $HNO_3$ and 1% HF.

(iii) a third calibration standard comprising La, Ce, Pr, Nd, S, Eu, Gd, Tb, Dy, Ho, Er, Tm, Yb, Lu, Sc, and Y, typically at concentrations between about 1 ppb and about 100 ppb for each of the recited elements; and preferably at concentrations between about 10 to about 20 ppb. One commercially available form for this standard is the Periodic Table Mix 3 for ICP available from Sigma-Aldrich Co. LLC. These elements are stored in about 5% $HNO_3$.

(iv) a fourth calibration standard comprising Os, typically at concentrations between about 1 and about 100 ppb, and preferably between about 10 to about 20 ppb. Os is stored in 10% v/v HCl.

(v) a fifth calibration standard comprising Hg, typically at concentrations between about 0.1 and about 10 ppb, and preferably between about 1 to about 2 ppb. Hg is stored in 10% v/v $HNO_3$.

(vi) a sixth calibration standard comprising Cl, typically at concentrations between about 1 and about 1000 ppm, and preferably between about 150 to about 300 ppm. Cl is stored in water.

(vii) a seventh calibration standard comprising Br, typically at concentrations between about 1 and about 100 ppb, and preferably between about 100 to about 200 ppb. Br is stored in water.

(viii) an eighth calibration standard comprising I, typically at concentrations between about 0.5 and about 50 ppb, and preferably between about 5 to about 10 ppb. I is stored in 1% TEA.

(ix) a ninth calibration standard comprising Na, Mg, Ca, K, S, P, Si, In and Cs, typically at concentrations of between about 1 and about 500 ppm for each of Na, Mg, Ca, S, and P, between about 0.1 and about 15 ppm for each of K and Si, and between about 1 and about 100 ppm for each of In and Cs; and preferably at concentrations between about 50 and about 150 ppm for each of Na and Mg, between about 100 and about 300 ppm for Ca, between about 20 and about 50 ppm for each of S and P, between about 1 and about 5 ppm for Si, between about 5 and about 8 ppm for K, and between about 10 and about 20 ppb for each of In and Cs.

According to yet embodiment, eleven or optionally twelve calibration standards are provided in two or three different concentrations. The eleven (and optional twelfth) standards are:

(i) a first calibration standard comprising Li, Be, B, Na, Mg, Al, K, Ca, V, Cr, Mn, Fe, Co, Ni, Cu, Zn, Ga, Ge, As, Se, Rb, Sr, Mo, Ag, Cd, Te, Ba, Tl, Pb, Bi, and U, typically at concentrations between about 5 ppb and about 50 ppm for each of the recited elements; and preferably at concentrations between about 10 to about 100 ppb for each of Ag, Al, Ba, Bi, Cd, Co, Cr, Cu, Ga, K, Li, Mg, Mo, Na, Ni, Pb, Rb, Sr, Tl, U, and V, between about 100 ppb to about 2 ppm for each of As, B, Be, Se, and Zn, and between about 1 ppm to about 10 ppm for Ca. One commercially available form for this standard is the Certipur® Certified Reference Material ICP multi-element standard VI available from Merck KGaA (Germany). These elements can be stored in about 5 to about 10% $HNO_3$.

(ii) a second calibration standard comprising Li, Be, B, Na, Mg, Al, K, Ca, V, Cr, Mn, Fe, Co, Ni, Cu, Zn, Ga, Ge, As, Se, Rb, Sr, Ag, Cd, Te, Ba, Tl, Pb, Bi, U, S, P, Si, In, and Cs, typically at concentrations between about 1 ppb and about 100 ppb for each of the recited elements; and preferably at concentrations between about 10 to about 50 ppb. One commercially available form for this standard is the Periodic Table Mix 1 for ICP, which is available from Sigma-Aldrich Co. LLC. The elements are stored in 10% $HNO_3$.

(iii) a third calibration standard comprising Ti, Ge, Zr, Nb, Mo, Ru, Rh, Pd, Sn, Sb, Hf, Ta, W, Re, Ir, Pt, and Au, typically at concentrations between about 1 ppb and about 100 ppb for each of the recited elements; and preferably at concentrations between about 10 to about 20 ppb. One commercially available form for this standard is the Periodic Table Mix 2 for ICP, which is available from Sigma-Aldrich Co. LLC. These elements are stored in 5% $HNO_3$ and 1% HF.

(iv) a fourth calibration standard comprising La, Ce, Pr, Nd, S, Eu, Gd, Tb, Dy, Ho, Er, Tm, Yb, Lu, Sc, and Y, typically at concentrations between about 1 ppb and about 100 ppb for each of the recited elements; and preferably at concentrations between about 10 to about 20 ppb. One commercially available form for this standard is the Periodic Table Mix 3 for ICP available from Sigma-Aldrich Co. LLC. These elements are stored in about 5% $HNO_3$.

(v) a fifth calibration standard comprising Os, typically at concentrations between about 1 and about 100 ppb, and preferably between about 10 to about 20 ppb. Os is stored in 10% v/v HCl.

(vi) a sixth calibration standard comprising Hg, typically at concentrations between about 0.1 and about 10 ppb, and preferably between about 1 to about 4 ppb. Hg is stored in 10% v/v $HNO_3$.

(vii) a seventh calibration standard comprising Cl, typically at concentrations between about 1 and about 700 ppm, and preferably between about 10 to about 300 ppm. Cl is stored in water.
(viii) an eight calibration standard comprising Br, typically at concentrations between about 1 and about 2000 ppb, and preferably between about 50 to about 1000 ppb. Br is stored in water.
(ix) a ninth calibration standard comprising I, typically at concentrations between about 0.5 and about 1000 ppb, and preferably between about 5 to about 400 ppb. I is stored in 1% TEA.
(x) a tenth calibration standard comprising Ti, typically at concentrations between about 30 and about 1000 ppb, and preferably between about 50 to about 500 ppb. Ti is stored in 2% v/v $HNO_3$.
(xi) a eleventh calibration standard comprising Na, Mg, Ca, K, S, Si, and P, typically at concentrations of between about 1 and about 500 ppm for each of Na, Mg, Ca, S, Si, and P; and preferably at concentrations between about 20 and about 150 ppm for each of Na and Mg, between about 10 and about 300 ppm for Ca, between about 5 and about 100 ppm for each of S and P, between about 5 and about 100 ppm for K, and between about 4 and 14 ppm for Si.
(xii) an optional twelfth calibration standard comprising K, typically at concentrations between about 100 to about 1000 ppm, and preferably between about 300 and about 700 ppm.

According to yet embodiment, ten or optionally eleven calibration standards are provided in two or three different concentrations. The ten (and optional eleventh) standards are:
(i) a first calibration standard comprising Li, Be, B, Na, Mg, Al, K, Ca, V, Cr, Mn, Fe, Co, Ni, Cu, Zn, Ga, Ge, As, Se, Rb, Sr, Mo, Ag, Cd, Te, Ba, Tl, Pb, Bi, and U, typically at concentrations between about 5 ppb and about 50 ppm for each of the recited elements; and preferably at concentrations between about 10 to about 100 ppb for each of Ag, Al, Ba, Bi, Cd, Co, Cr, Cu, Ga, K, Li, Mg, Mo, Na, Ni, Pb, Rb, Sr, Tl, U, and V, between about 100 ppb to about 2 ppm for each of As, B, Be, Se, and Zn, and between about 1 ppm to about 10 ppm for Ca. One commercially available form for this standard is the Certipur® Certified Reference Material ICP multi-element standard VI available from Merck KGaA (Germany). These elements can be stored in about 5 to about 10% $HNO_3$.
(ii) a second calibration standard comprising Ti, Ge, Zr, Nb, Mo, Ru, Rh, Pd, Sn, Sb, Hf, Ta, W, Re, Ir, Pt, and Au, typically at concentrations between about 1 ppb and about 100 ppb for each of the recited elements; and preferably at concentrations between about 10 to about 20 ppb. One commercially available form for this standard is the Periodic Table Mix 2 for ICP, which is available from Sigma-Aldrich Co. LLC. These elements are stored in 5% $HNO_3$ and 1% HF.
(iii) a third calibration standard comprising La, Ce, Pr, Nd, S, Eu, Gd, Tb, Dy, Ho, Er, Tm, Yb, Lu, Sc, and Y, typically at concentrations between about 1 ppb and about 100 ppb for each of the recited elements; and preferably at concentrations between about 10 to about 20 ppb. One commercially available form for this standard is the Periodic Table Mix 3 for ICP available from Sigma-Aldrich Co. LLC. These elements are stored in about 5% $HNO_3$.
(iv) a fourth calibration standard comprising Os, typically at concentrations between about 1 and about 100 ppb, and preferably between about 10 to about 20 ppb. Os is stored in 10% v/v HCl.
(v) a fifth calibration standard comprising Hg, typically at concentrations between about 0.1 and about 10 ppb, and preferably between about 1 to about 4 ppb. Hg is stored in 10% v/v $HNO_3$.
(vi) a sixth calibration standard comprising Cl, typically at concentrations between about 1 and about 700 ppm, and preferably between about 10 to about 300 ppm. Cl is stored in water.
(vii) a seventh calibration standard comprising Br, typically at concentrations between about 1 and about 2000 ppb, and preferably between about 50 to about 1000 ppb. Br is stored in water.
(viii) an eighth calibration standard comprising I, typically at concentrations between about 0.5 and about 1000 ppb, and preferably between about 5 to about 400 ppb. I is stored in 1% TEA.
(ix) a ninth calibration standard comprising Ti, typically at concentrations between about 30 and about 1000 ppb, and preferably between about 50 to about 500 ppb. Ti is stored in 2% v/v $HNO_3$
(x) a tenth calibration standard comprising Na, Mg, Ca, K, S, P, Si, In and Cs, typically at concentrations of between about 1 and about 500 ppm for each of Na, Mg, Ca, S, and P, and between about 1 and about 100 ppb for each of In and Cs; and preferably at concentrations between about 20 and about 150 ppm for each of Na and Mg, between about 10 and about 300 ppm for Ca, between about 5 and about 100 ppm for each of S and P, between about 5 and about 100 ppm for K, between about 1 and about 14 ppm for Si, and between about 10 and about 20 ppb for each of In and Cs.
(xi) an optional eleventh calibration standard comprising K, typically at concentrations between about 100 to about 1000 ppm, and preferably between about 300 and about 700 ppm.

Using an internal standard and a plurality of calibration standards as described above, in combination with an ICP-MS device of the type described above, the present invention affords a method for simultaneously detecting absolute concentrations of a plurality of elements in a liquid sample. This method includes: introducing a known concentration of the internal standard into each of the plurality of calibration standards, a blank standard (e.g., ultrapure water with 1% $HNO_3$), and a liquid sample to be tested; introducing each of the plurality of calibration standards, the blank standard, and the liquid sample to be tested individually into an inductively coupled plasma mass spectrometer to simultaneously detect one or more ionization products of elements present in each of the plurality of calibration standards, the blank standard, and the liquid sample to be tested; and determining an absolute concentration of the one or more detected elements in the liquid sample relative to the one or more detected ionization products of elements in the plurality of calibration standards.

To achieve sound values for elements in each concentration for each calibration standard, blank, and liquid sample, the respective solution is flushed into the ICP-MS for at least about 60 seconds before measurement (known as "preflush"). In certain embodiments, the preflush can be carried out for at least about 75 seconds or even at least about 90 seconds for liquid samples, and even at least about 2 min for the blank. Multiple (n) consecutive measurements can be made and then a mean value of each isotope per liquid sample can be established. With a minimum 60 sec preflush and the three measurements per liquid sample, a total solution volume of at least about 4 mL should be used. For longer preflush routines and larger numbers of liquid sample analyses (e.g., n is four, five, six, seven, or more), then larger total solution volumes should be used. The minimum standard pipetting volume is 100 resulting in a total standard/sample volume of 10 mL.

As explained above, the output of the ICP-MS is in cps, which is converted to absolute concentration measurements (by the ICP-MS processor) using the stored regression formulae associated with each element of the calibration standards. As such, the ICP-MS device will output the detected absolute concentration of each detected element.

According to this aspect of the invention, the liquid sample can be from any of a variety of sources including water samples from, e.g., bottled water, a drinking water source (tap or well or drinking fountain), a body of water, a glacier, a snowpack, runoff from a manmade structure such as a home or other building, runoff from a field, wastewater discharge, a sewage treatment facility, and various forms of precipitation including, among others, rain, fog, slush, hail, snow, grapple, freezing rain, and sleet. Without limitation to the foregoing list of water samples, any aqueous sample can be tested where the sample used for testing contains a solution of about 1% or less of total dissolved solids ("TDS"). Thus, a directly obtained sample containing higher than about 1% TDS can be diluted with ultrapure water to achieve a TDS of not more than about 1%.

As alternatives, the liquid sample can be in the form of a urine sample, saliva sample, homogenized tissue sample, (plasma, serum or whole) blood sample, wine sample, beer sample, liquor sample, milk sample, or any other aqueous beverage or biofluid that can be made up (or diluted with ultrapure water) to afford a TDS of not more than about 1%.

In most instances it is desirable to pre-treat the liquid sample with the addition of an $HNO_3$ solution (about 1%) prior to introducing a known volume of the internal standard to facilitate element release from sample tubes. Every liquid sample therefore consists of the sample itself, 1% $HNO_3$, and the internal standards.

As used during the above method, the blank standard as introduced into the ICP-MS device includes about 97.5% v/v ultrapure water, about 1.5% v/v $HNO_3$, and about 1% v/v of the internal standard composition.

Based on the results of the method, it is possible to compare the absolute concentration of the one or more detected elements (i.e., ionization products thereof) with a guideline standard (e.g., a safety standard identifying the highest concentration of the one or more elements considered safe for human or veterinary use or consumption).

By way of example, drinking water sources should not contain excessive amounts of lead or mercury, or other heavy metal elements. Thus, it is possible to assess whether or not a drinking water source contains water that is safe to consume. In this example, the recited method steps are carried out on a first water sample obtained from a water source; and then repeated on a second water sample obtained from the water source at a later point in time. In this example, the second sample can be obtained after treating the water source to alter the elemental concentration in water obtained from the source.

In another example, water samples can be obtained before, during, and after certain human activities. Non-limiting examples of such activities include surface development, mining, farming, and timber harvesting.

In another embodiment, the guideline standard may represent an elemental profile for a particular water source, wine source, etc. As such, the method of the present invention can be used to determine the provenance of the liquid sample by comparing the determined, absolute concentration of the one or more detected elements in the liquid sample to an absolute concentration of the one or more detected elements in a reference product of established provenance; and determining whether the liquid sample is comparable to the reference product of established provenance.

A further aspect of the invention relates to a kit that is suitable for carrying out the method of simultaneously detecting absolute concentrations of a plurality of elements in a liquid sample. The kit includes an internal standard as described above, a plurality of calibration standards as described above, and optionally instructions for performing the method as described above.

EXAMPLES

The following examples are provided to illustrate embodiments of the present invention but are by no means intended to limit its scope.

Materials and Methods for Examples 1-4

Instrumentation

All measurements were performed with a SEPCTRO MS 01 (SPECTRO Analytical Instruments GmbH, Kleve, Germany) si-ICP-MS. The specifics of its detector (4,800 detector elements) allow for the detection of all isotopes in the relevant mass spectrum from $^6Li$ to $^{238}U$ (Ardelt et al., 2013). Fluid samples are introduced by pneumatic nebulization with argon as carrier gas, using a SeaSpray Nebulizer and nickel sampler and skimmer cones. Typical operating parameters are shown in Table 1.

TABLE 1

| si-ICP-MS operating conditions and parameters. | | | |
|---|---|---|---|
| Spectrometer | SPECTRO MS1 | Elements measured | 71 |
| Nebulizer | SeaSpray | Preflush [sec] | 155-90 |
| Spray chamber | Cyclonic | Sample aspiration rate [mL/min] | 1-2 |
| Interface | Ni sampler and skimmer cones | Number of measurements | 3 |
| Plasma power [W] | 1465 | Total Time [s] | 30 |
| Extractor/Lens voltage [V] | 880 | Replicate Read time [s] | 10 |
| Coolant flow [L/min] | 8.0 | Base Interval/Dwell time [ms] | 10 |
| Auxiliation flow [L/min] | 2.6 | | |
| Nebulizer flow [L/min] | 0.88 | Scanning mode | Threshold |
| Sweeps/Readings | NA | Peak Pattern Resolution [amu] | 1 point |

Optimization

Prior to making measurements, the SEPCTRO MS was optimized by a routine to provide maximum sensitivity over the entire mass/ratio range with reasonably low levels of oxide ion formation (BaO+/Ba+) and for peak shape (Ardelt et al., 2013). The optimization routine was carried out using SPECTRO MS software, Mass Analyzer Vision (v. 1.32.1405) and employ of the MERCK VI multi-element standard (Merck Multiemlementstandard VI, Merck Darmstadt, Germany), 20 ppb, diluted 1:500 (v/v) with ultrapure water and acidified with ultrapure $HNO_3$ to 1% (v/v). When alcoholic beverage samples were analyzed, 0.9% (v/v) dehydrated ethanol ($C_2H_5OH$ with less than 0.1% (v/v) water, DNase, and RNase non-detected) to match the physical properties of the alcoholic samples.

Consumables

Reagents:

Throughout the entire study, all standards, samples and other solutions (wash, rinse, etc.) were prepared with de-ionized ultrapure water (>18.2MΩ cm) from a MilliQ-Element system designed for inorganic ultra-trace analysis (Millipore, Milford, Mass., USA) and acidified to 1% (v/v) (Fernandez-Turiel et al., 2000; Louie et al., 2012) with ultrapure 65% $HNO_3$ (analytical-reagent grade, Merck, Darmstadt, Germany).

Containers and Pipettes:

Containers used in ICP-MS analysis must be very clean, lockable, and made of high density polyethylene (HDPE) (Fernandez-Turiel et al., 2000), certified to be DNase/RNase and pyrogen free. However, manufacturing processes may leave chemical residues, thus, before containers were used, either for holding samples, standards, or blanks, they were cleaned with $HNO_3$ (Gonzálvez et al., 2008). Containers were fully filled with 1-2% (v/v) ultrapure $HNO_3$ diluted with ultrapure water and left standing for a minimum of 24 h, after which the containers were turned 180° so that the entire inside of the container would have been exposed to ultrapure $HNO_3$ for at least 24 h. Thereafter, the ultrapure $HNO_3$ was discharged and the containers were rinsed with ultrapure water. The rinse water was completely discharged, including all droplets, and the cap was screwed back on tightly until use. The containers were not dried on the inside with any towel or wipe.

Pipette tips were made of highly purified HDPE and met EN ISO 86655 requirements.

Standards and Sample Preparation

Best results are established when the minimum standard pipetting volume is 100 μL, resulting in a total standard or sample volume of 10 mL. High pipetting precision was achieved by using the pipetting robot ANDREW (Andrew Allience S. A., Geneva, Switzerland). Preparation was most accurate when all fluids were pipetted at room temperature.

Internal Standards:

To account for day-to-day variability in instrument conditions (instrument drift and physical interferences) during the time of measurement (DeBoer et al., 1996), internal standards were introduced into the blank sample, each calibration standard, the standard reference material and controls, and into each test sample, at identical concentrations. Internal standards are typically elements thought not to occur in the test sample and thus not being calibrated for; these are typically elements with only one isotope, or one isotope having a dominant natural abundance. Furthermore, the internal standards should be in close proximity (in terms of their atomic number) to the measured and calibrated elements.

To represent the entire mass spectrum, it was found best to use $^6Li$, $^{103}Rh$ (Stezenbach et al., 1994; Goullé et al., 2005; D'Ilio et al., 2006; Krachler and Shotyk, 2009; Ding et al., 2012; Bressy et al., 2013; Šelih et al., 2014) and $^{232}Th$ as internal standards; thus $^6Li$, $^{103}Rh$ and $^{232}Th$ could not be measured in test samples. Internal standard concentrations of 10 mg/L $^6Li$, 2 mg/L $^{103}Rh$ and 2 mg/L $^{232}Th$ (LiRhTh) were used in order to overwhelm any traces of these elements/isotopes that might conceivably be found in a sample. $^6Li$ was used for elements in the m/z range of 7 (Li) to 54 (Fe), $^{103}Rh$ for the m/z ranges 55 (Mn) to 159 (Tb), and $^{232}Th$ for elements within m/z ratios of 161 (Dy) to 238 (U). As an exception, $^{103}Rh$ was used for $^{51}V$ due to better results.

Nevertheless, when rhodium and/or thorium are of special interest, $^6Li$ was used and $^{89}Y$ was exchanged for $^{103}Rh$ and/or $^{159}Tb$ for $^{232}Th$ (LiYTh, LiYTb, LiRhTb). Concentrations for $^{89}Y$ and $^{159}Tb$ were 2 mg/L, respectively. Adjusting the internal standards leads to different coverages of elements by the internal standards: for LiYTh, $^6Li$ is used for elements in the m/z range from 7 (Li) to 56 (Fe), $^{89}Y$ for the m/z range from 59 (Co) to 157 (Gd) and $^{232}Th$ for elements in the m/z range from 159 (Tb) to 238 (U). For LiYTh, $^6Li$ is used for elements in the m/z range from 7 (Li) to 56 (Fe), $^{89}Y$ for the m/z range from 59 (Co) to 127 (I) and $^{159}Tb$ for 133 (Cs) to 238 (U). When only $^{232}Th$ is exchanged (LiRhTb), element ranges remain for $^6Li$ from 7 (Li) to 52 (Cr), and change for $^{103}Rh$ to m/z ranges from 54 (Fe) to 103 (Rh) and for $^{159}Tb$ from 106 (Pd) to 238 (U).

Blank Standard:

The blank standard is made of ultrapure water, 1% (v/v) ultrapure $HNO_3$ to facilitate element release from sample tube surfaces (Louie et al., 2012), and the internal standards LiRhTh.

Calibration Standards:

Calibration standards were designed to calibrate all relevant elements between $^6Li$ and $^{238}U$ (Li, Be, B, Na, Mg, Al, Si, P, S, Cl, K, Ca, Sc, Ti, V, Cr, Mn, Fe, Co, Ni, Cu, Zn, Ga, Ge, As, Se, Br, Rb, Sr, Y, Zr, Nb, Mo, Ru, Pd, Ag, Cd, In, Sn, Sb, Te, I, Cs, Ba, La, Ce, Pr, Nd, Sm, Eu, Gd, Tb, Dy, Ho, Er, Tm, Yb, Lu, Hf, Ta, W, Re, Os, Ir, Pt, Au, Hg, Tl, Pb, Bi, U). See Table 2 below.

Each element is commercially available as a single element standard, however, grouping and measuring multiple elements together is far more economical and preferred. The 71 measureable elements were grouped into six standards:

(i) The ICAL-Group (ICAL): ICAL is a 30 element multi standard in 5-10% (v/v) $HNO_3$ (Certipur® Certified Reference Material ICP multi-element standard VI: Merck KGaA, Germany) (Leonhard et al., 2002; Goullé et al., 2005) which contains Li, Be, B, Na, Mg, Al, K, Ca, V, Cr, Mn, Fe, Co, Ni, Cu, Zn, Ga, Ge, As, Se, Rb, Sr, Mo, Ag, Cd, Te, Ba, Tl, Pb, Bi, and U in various concentrations. This multi standard is also used to calibrate the ICP-MS.

(ii) The Mix1-Group (Mix1): Mix1 elemental composition is very similar to the ICAL-group, with the additional elements S, P, Si, In, Cs, but without Mo. These elements come together as Periodic Table Mix 1 for ICP (Trace Cert® Sigma-Aldrich Production GmbH, Buchs, Switzerland). The elements are stored in 10% (w/w) $HNO_3$.

(iii) The Mix2-Group (Mix2): Mix2 has an elemental composition of Ti, Ge, Zr, Nb, Mo, Ru, Rh, Pd, Sn, Sb, Hf, Ta, W, Re, Ir, Pt and Au, and needs special storage conditions (5% (w/w) $HNO_3$ and 1% (w/w) HF). These are available as Periodic Table Mix 2 for ICP (Trace Cert® Sigma-Aldrich Production GmbH, Buchs, Switzerland).

(iv) The Rear Earths- or Mix3-Group (Mix3): Mix3 consists of elements belonging to the lanthanide series (La, Ce, Pr, Nd, Sm, Eu, Gd, Tb, Dy, Ho, Er, Tm, Yb and Lu), as well as scandium (Sc) and yttrium (Y). They are contained in the Periodic Table Mix 3 for ICP (Trace Cert® Sigma-Aldrich Production GmbH, Buchs, Switzerland), in 5% (w/w) $HNO_3$.

(v) The Single Element-Group: Single Element-Group standards are all single elements and are either not present in any of groups 1-4, or are required in very different concentrations to enable precise measurement. Elements that belong to this group are: Cl and Br (in $H_2O$), K (in 0.1% v/v $HNO_3$), Ti (in 2% v/v $HNO_3$), Hg (in 10% v/v $HNO_3$), Os (in 10% v/v HCl) and I (in 1% TEA) (all solutions acquired from: Inorganic Ventures, Christiansburg, Va., U.S.A). These elements (K only for saliva samples) are used as single element standards.

(vi) The Multi-Group (Multi): all elements within it are produced by Inorganic Ventures as single elements and are mixed into one solution in the lab to account for higher concentration needs of P, S (in $H_2O$), Na, Mg, Ca and K (in 0.1% v/v $HNO_3$) and Si (in tr. $HNO_3$ and tr. HF), as well as In (in 2% v/v $HNO_3$) and Cs (in 7% v/v $HNO_3$), in the case of not using the Mix1-Group (Mix1).

All elements, whether in mixes or single element standards, are certified reference materials that are directly traceable to top the corresponding NIST Standard Reference Material (SRM)®.

standard refer to Ag, Al, Ba, Bi, Cd, Co, Cr, Cu, Ga, K, Li, Mg, Mn, Mo, Na, Ni, Pb, Rb, Sr, Te, Tl, U and V. These elements have an original concentration of 10 ppm, whereas ICAL contains 100 ppm of As, B, Be, Fe, Se and Zn, as well as 1,000 ppm of Ca, and their respective concentrations in the final calibration standards differ respectively.

Mix1 calibration standards consist of 10 and 50 ppb, whereas Mix2, Mix3 and Os calibration standards are made up into concentrations of 10 and 20 ppb.

Cl calibration standards are made to 150 and 300 ppm for environmental water and biofluid samples, 10 and 20 ppm for wine samples, and 10 and 50 ppm for bottled water samples. In addition, 5 and 10 ppm Cl standards was used to account for chlorine interference on potassium in all but the biofluid and bottled water samples.

Concentration of Br standards also vary depending on the nature of the samples: for environmental water bromine is calibrated for 100 and 200 ppb, for biofluids 500 and 1,000 ppb, for wine samples 50 and 100 ppb, and for bottled water 100 and 250 ppb.

When analyzing biofluids, additional K single element standards were used consisting of 300 and 700 ppm.

Although Ti is included in the Mix2 calibration standard (at 10 and 20 ppb) an additional single element Ti standard

TABLE 2

List of calibration standards used.

| | Environ. + Tap | | Saliva/blood/urine | | Wine/beer/milk | | BW | |
|---|---|---|---|---|---|---|---|---|
| Mix standards | | | | | | | | |
| ICAL | 10, 20, 100 ppb | | 10, 20, 100 ppb | | 20, 100, 200 ppb | | 10, 20, 100 ppb | |
| Mix1 | 10 ppb | 50 ppb | 10 ppb | 50 ppb | 10 ppb | 50 ppb | 10 ppb | 50 ppb |
| Mix2 | 10 ppb | 20 ppb | 10 ppb | 20 ppb | 10 ppb | 20 ppb | 10 ppb | 20 ppb |
| Mix3 | 10 ppb | 20 ppb | 10 ppb | 20 ppb | 10 ppb | 20 ppb | 10 ppb | 20 ppb |
| Single element standards | | | | | | | | |
| Cl | 150 ppm | 300 ppm | 150 ppm | 300 ppm | 10 ppm | 20 ppm | 10 ppm | 50 ppm |
| Br | 100 ppb | 200 ppb | 500 ppb | 1000 ppb | 50 ppb | 100 ppb | 100 ppb | 250 ppb |
| K | | | 300 pm | 700 ppm | | | | |
| Ti | 100 ppb | | 100 ppb | | 50 ppb | 100 ppb | 500 ppb | |
| Hg | 1 ppb | 4 ppb | 1 ppb | 4 ppb | 1 ppb | 2 ppb | 1 ppb | 2 ppb |
| Os | 10 ppb | 20 ppb | 10 ppb | 20 ppb | 10 ppb | 20 ppb | 10 ppb | 20 ppb |
| I | 5 ppb | 10 ppb | 100 ppb | 400 ppb | 2 ppb | 5 ppb | 5 ppb | 10 ppb |
| Multi standard | | | | | | | | |
| Ca | 300 ppm | 100 ppm | 50 ppm | 100 ppm | 20 ppm | 50 ppm | 10 ppm | 50 ppm |
| K | 12 ppm | 8 ppm | 12 ppm | 8 ppm | 50 ppm | 100 ppm | 30 ppm | 9 ppm |
| Mg | 50 ppm | 150 ppm | 50 ppm | 150 ppm | 30 ppm | 60 ppm | 20 ppm | 100 ppm |
| Na | 50 ppm | 150 ppm | 50 ppm | 150 ppm | 20 ppm | 40 ppm | 50 ppm | 150 ppm |
| P | 20 ppm | 50 ppm | 50 ppm | 100 ppm | 20 ppm | 50 ppm | 5 ppm | 20 ppm |
| S | 20 ppm | 50 ppm | 20 ppm | 50 ppm | 30 ppm | 60 ppm | 5 ppm | 20 ppm |
| Si | 12 ppm | 8 ppm | 12 ppm | 8 ppm | 4 ppm | 8 ppm | 8 ppm | 14 ppm |

All standards were diluted with ultrapure water, contain 1% ultrapure $HNO_3$ and the internal standard LiRhTh. For the analysis of alcohol containing samples, 0.9% dehydrated alcohol was added to every standard without changing the element concentration.

The six groups can be used in one of two possible combination sets: 1) ICAL, Mix1, Mix2, Mix3, the Multi and Os, Hg, I, Ti, Cl, Br, (and K for saliva) as single standards, or 2) ICAL, Mix2, Mix3, the Multi with added In and Cs, and Os, Hg, I, Ti, Cl, Br, (and K for saliva) as single standards.

The six groups result in 11 (12 for biofluids) standards, with at least two concentrations of each of the calibration standards. Concentration of the calibration standards were chosen with regard to the expected concentrations in test samples (see Table 2).

The ICAL calibration standard is made up to 10, 20 and 100 ppb, and to 20, 100 and 200 ppb for wine samples. Note, however, that the ICAL standard has differently concentrated elements. The concentrations stated here for the at 100 ppb was used to ensure a high standard correlation regression. This was used for all but the wine samples; in the wine samples, 50 and 100 ppb was used.

The calibration standards of Hg are made into concentrations of 1 and 2 ppb for the blood and urine samples, wine and bottled water, and 1 and 4 ppb for environmental water (incl. tap water) and saliva.

The Multi calibration standard changes, with regard to the sample type are reflected in Table 2: for body fluids, the Multi standard consists of the following concentrations: 50 and 100 ppm for Ca, 50 and 150 ppm for Na and Mg, 8 and 12 ppm for K and Si, 20 and 50 ppm for S and 50 and 100 ppm for P. For water samples, concentrations of Ca were changed to 100 and 300 ppm, and concentrations of P were changed to 20 and 50 ppm. For wine samples, the Multi standard contains 20 and 50 ppm Ca, 50 and 100 ppm K, 30 and 60 ppm Mg, 20 and 40 ppm Mg, 20 and 50 ppm P, 30 and 60 ppm S, and 4 and 8 ppm Si. For bottled water samples, concentrations of 10 and 50 ppm Ca, 3 and 9 ppm K, 20 and 100 ppm Mg, 20 and 150 ppm Na, 5 and 20 ppm P and S, as well as 8 and 14 ppm Si were selected.

When Cs and In are added as single element standards instead of Mix 1, they are added to the Multi element calibration standard with 10 and 20 ppb.

Each calibration standard contains ultrapure water, 1% ultrapure $HNO_3$ to facilitate element release from sample tube surfaces, and the internal standards LiRhTh at 100 ppb Li and 20 ppb Rh and Th. In the case of Mix2 and Os calibration standards (see below), 0.5% ultrapure HCl (Merck, Darmstadt, Germany) was added to ensure element stability.

For the analysis of alcoholic beverages (wine, beer), 0.9% (v/v) dehydrated ethanol ($C_2H_5OH$ with less than 0.1% (v/v) water, DNAse and RNAse non-detected) was added to all calibration standards to match the alcohol content of the diluted sample material as closely as possible. This eliminated effects of different physical properties of the liquids, which are possibly generated by the presence of alcohol. Same matrix for cal and sample.

Standards with elemental concentrations of less than 20 ppb were prepared on the day of measurement to avoid degradation. Ideally, Mix2 and Os calibrations standards should be prepared immediately prior to measurement.

Reference Material and Controls.

The Standard Reference Material (SRM) 1640a by NIST (trace elements in natural water) was used to evaluate the method and confirm that it is reproducible over time and between different laboratories.

SRM 1640a consist of acidified (2% $HNO_3$) spring water with mass fractions and mass concentrations assigned for 29 elements, 22 of which were gravimetrically added: Be, B, Al, V, Cr, Mn, Fe, Co, Ni, Cu, Zn, As, Se, Sr, Mo, Ag, Cd, Sb, Ba, Tl, Pb, U. The certified values of these elements range between 1.6 and 300.7 ppb. Only the internal standard LiRhTh was added, at the same concentrations as for the calibration standards.

The NIST reference material was measured after the calibration standards/before and after all samples. To furthermore account the accuracy of measurements, ICAL at 20 ppb (100 ppb for wine), Mix 2 and Mix 3 at 10 ppb, Hg at 1 ppb, as well as the lower concentrated Multi standard were measured at least every 10 samples.

With the exception of Be and Tl, which have concentrations below the detection limit of the method herein, the objective was to reproduce given values ±20%.

Sample Preparation and Procedures.

The method was tested on 15 different types of aqueous sample, which include environmental water (tap, well, rain, lake, river, sea, and snow), beverages (bottled water, wine, beer, and milk), and biological fluid samples (plasma, blood, saliva, and urine) (Table 4). All samples were collected directly into the prepared HDPE containers (15 and 50 mL centrifuge tubes, Fischer Scientific, U.S.A.), without any intermediate container. The samples were not filtered, refrigerated or acidified for the purpose of stabilizing molecules such as phosphates, nitrates, etc., since the elemental composition will not change after sampling. Wine and biofluid samples were refrigerated between sampling and analysis.

When dilution was required, samples were diluted with ultrapure water. For analysis, all (diluted) samples contain 1% (v/v) $HNO_3$ and internal standards were added (1:100).

Nitric acid prevents elements and chemicals from adhering to the container walls, and ensures that the total amount of elements/chemicals will be introduced into the si-ICP-MS, and hence measured. It has been reported that Hg is likely to be volatized and adsorbed onto the inner walls of HDPE containers (Louie et al., 2012), and that therefore chloride should be added to the sample to prevent the loss of Hg (Feldman, 1974).

In general, samples should not contain more than 1,000 ppm total dissolved content so as not to clog the sample injection orifices and to guarantee accurate measurements. If they do, or are suspected to, sample dilutions must be made accordingly. When elements in samples exceed calibrated concentration values, dilution is also recommended.

Water Samples.

Except for sea water, water samples were not diluted. Tap water was collected as first water in the morning (0 min) and after 5 min of water discharge. The sea water samples were diluted 1:20 and 1:40 (v/v) (Leonhard et al., 2002) to quantify elements in low and high concentrations.

Beverage Samples.

The wine samples were diluted 1:15 (v/v) (Gonzálvez et al., 2008; Šelih et al., 2014; Taylor et al., 2003) because of the high content of dissolved solids. The beer samples were shaken multiple times, then heated in a bain-marie for 20 min at 90° C. to eliminate carbon dioxide and subsequently diluted 1:5 and 1:10 (v/v). The milk samples were diluted 1:25 (v/v), as suggested by Mohd-Taufek et al. (2016), because of the high content of dissolved solids. The diluted milk samples were vortexed for 2 min and then let stand to settle. The supernatant was used for analysis. Milk and beer were collected from local supermarkets, and the wine was purchased in liquor retail stores in the United States. Bottled water samples were not diluted.

Biofluid Samples.

All biofluid biological samples were collected in the morning on the same day, by one male and one female test person. All samples were stored at 4° C. until analysis.

In contrast to Staff et al. (2014) and Nriagu et al. (2006), who used a saliva collecting device, the saliva was instead collected directly into a prepared sample tube to avoid contamination from the saliva collecting device itself and its containing buffers. The saliva was collected in the morning prior to eating, rinsing, and tooth brushing. In previous studies, saliva has been prepared in two main ways, with (Kim et al., 2010) and without microwave digestion (Vaughan et al., 1991; Nriagu et al., 2006; Staff et al., 2014; Dame et al., 2015). Here, the saliva samples were acidified with ultrapure $HNO_3$ (Vaughan et al., 1991; Nriagu et al., 2006; Dame et al., 2015) and the samples allowed to stand for 48 h so that the undissolved solids (mostly cheek lining cells) could settle to the bottom of the sample tube (alternatively, samples can be centrifuged at 4,000 rpm for 40 min). The supernatant was then diluted 1:10 and 1:20 (v/v).

Midstream urine samples were collected directly into 50 mL HDPE containers. The samples were diluted with 1% (v/v) $HNO_3$ and stored at 4° C. For analysis, the urine samples were diluted 1:2 (v/v) in contrast to published dilutions of 1:5 or 1:10 (Goullé et al., 2005), to ensure full recording of low-concentration elements.

A fasting, venous blood sample was collected into 2 EDTA blood collection vials via a pyrogen free blood collection set. The first collection vial was discharged to minimize contamination from the blood collection set (Heitland et al., 2006). Blood from the second collection vial was separated (in 15 mL HDPE containers) to obtain two sub-samples: whole blood and plasma. For the whole blood samples, 2 mm steel metal beads, washed overnight in ultrapure 2% (v/v) HNO3) were added to the samples and the whole blood samples vortexed at about 2,000 rpm for 30 sec. in 4-6 repeating cycles. The beads were removed and the samples then diluted 1:100. For the plasma samples, the blood was centrifuged for 20 minutes at 1500 RCF. The supernatant plasma was diluted 1:10 (v/v) (male) and 1:20 (v/v) (female) with 1% (v/v).

Measurement Procedure

The si-ICP-MS was optimized and calibrated daily (as described above), before making quantitative measurements.

To achieve sound values for elements in each concentration for the blank, each calibration standard, each control, and the sample, the respective solution was flushed into the si-ICP-MS for at least 30 seconds after reaching the plasma via the sample tubing from the autosampler (known as "preflush"). Three aliquots are measurements and a mean value of each measured isotope was established (isotopes monitored are given in Table 3 below). A total solution volume of 4 mL or greater was used at the minimum sample aspiration rate (1 ml/min). The volume may vary depending on instrument parameters such as pump speed, nebulizer flow, preflush time and tube lengths. The overall time per one sample analyses was about 5 minutes. The controls were analyzed after every $10^{th}$ sample, and the NIST SRM was analyzed before and after the unknown samples of each run.

Between the introduction of the blank, each calibration standard, sample, SRM and ICAL, the instrument was rinsed with an ultrapure 1-2% (v/v) $HNO_3$ for 120 sec (De Boer et al., 1996)(for water based samples) to 4 min (milk and blood samples), or longer if needed.

Generally, the si-ICP-MS produces stable data over several hours and up to 60 samples were measured after the set of calibration standards, resulting in approximately 7 hours per run. This time can vary greatly based on the time of rinse and preflush or the number of aliquots analyzed.

TABLE 3

Measured Isotopes

| Element | Isotope(s) |
|---|---|
| Li | 7* |
| Be | 9* |
| B | 10, 11* |
| Na | 23* |
| Mg | 24* |
| Al | 27* |
| Si | 28* |
| P | 31* |
| S | 34* |
| Cl | 35*, 37 |
| K | 39* |
| Ca | 42, 43, 44* |
| Sc | 45* |
| Ti | 49* |
| V | 51* |
| Cr | 50, 52*, 53 |
| Mn | 55* |
| Fe | 54*, 57 |
| Co | 59* |
| Ni | 58, 60*, 62 |
| Cu | 63*, 65 |
| Zn | 66*, 67, 68 |
| Ga | 69*, 71 |
| Ge | 72*, 73, 74 |
| As | 75* |
| Se | 77, 78, 82* |
| Br | 79, 81* |
| Rb | 85* |

TABLE 3-continued

Measured Isotopes

| Element | Isotope(s) |
|---|---|
| Sr | 88* |
| Y | 89* |
| Zr | 90*, 91 |
| Nb | 93* |
| Mo | 97, 98* |
| Ru | 99, 101*, 102 |
| Pd | 105, 108* |
| Ag | 107, 109* |
| Cd | 111, 112*, 114 |
| In | 115* |
| Sn | 117, 118 119, 120* |
| Sb | 121*, 123 |
| Te | 126, 128*, 130 |
| I | 127* |
| Cs | 133* |
| Ba | 135, 138* |
| La | 139* |
| Ce | 140* |
| Pr | 141* |
| Nd | 143, 144*, 145, 146 |
| Sm | 147, 149, 152* |
| Eu | 151*, 153 |
| Gd | 155, 157, 158* |
| Tb | 159* |
| Dy | 161, 162, 631*, |
| Ho | 165* |
| Er | 166*, 167 |
| Tm | 169* |
| Yb | 171, 172, 173, 174* |
| Lu | 175* |
| Hf | 177, 178, 179* |
| Ta | 181* |
| W | 182, 183, 184*, 186 |
| Re | 185, 187* |
| Os | 188, 189, 190, 192* |
| Ir | 191, 193* |
| Pt | 194, 195*, 196 |
| Au | 197* |
| Hg | 200, 201, 202* |
| Tl | 203, 205* |
| Pb | 206, 207, 208* |
| Bi | 209* |
| U | 238* |

*Isotopes typically chosen for analysis

Analysis Procedure

Measured isotope peaks and backgrounds, of the calibration standards and samples, were manually defined. Readings of the blank and at least two calibrations standards are plotted to achieve a regression line with a correlation coefficient above, or equal to $R^2=0.996$, higher than suggested by Goullé et al. (2005). The regression also factors in possible interferences that occur at the respective isotopes. All post-measurement analyses were carried out using SPECTRO MS software, Mass Analyzer Vision (v. 1.32.1405).

When elemental concentration was measured on multiple isotopes (of one element), the isotope with the lowest relative standard deviation was selected. Mean values, relative standard deviation, and detection limits were recorded for each element and given in Table 5.

TABLE 4

| Environmental Water Samples | Location | GPS Coordinates |
|---|---|---|
| *Aqueous Samples* | | |
| Bottled water | | |
| Fiji Natural Artesian Water | Yaqara, Fiji | N/A |
| Gerolsteiner Mineral Water | Gerolstein, Germany | N/A |
| Tap water | | |
| (0- and 5-min) | Middletown, NY | Private home |
| Well water | | |
| Well 2 | Fresno, CA | 36°39'13"N, 119°39'49"W |
| Well 3 | Fresno, CA | 36°38'57"N, 119°37'51"W |
| Snow | | |
| Lassen Volcanic National Park | Lassen Volcanic NP, CA | 40°28'27.3"N, 121°30'21.7"W |
| Crater Lake National Park | Crater Lake NP, CA | 42°54'32"N, 122°04'25"W |
| Rain water | | |
| Bathsheba | Bathsheba, Barbados | 13°12'42.18"N, 9°31'4.46"W |
| Beijing | Beijing, PR China | 39°41'21"N, 115°55'23"E |
| Lake water | | |
| Lake Canandaigua | Canandaigua Lake State Marine Park, NY | 42°52'32.40"N, 7°16'36.50"W |
| Lake Baikal | Khuzhir, Irkutsk Oblast, Russia | 53°12'11"N, 107°20'27"E |
| River water | | |
| Delaware River | Pleasant Park Hill, PA | 40°2'27.51"N, 4°59'31.04"W |
| Nidda | Frankfurt, Germany | 50°9'46.10"N, 8°39'7.99"E |
| Sea water | | |
| Miami Beach | Oistins, Barbados | 13°3'39.86"N, 9°32'25.35"W |
| NJ Shore | Sea Isle City, NJ | 39°11'34.4"N, 74°39'23.7"W |
| *Beverage samples* | | |
| Wine | | |
| Schola Sarmenti Roccamora 2013, (Negroamaro grape) | Southern Italian region of Puglia | 40°10'27.46"N, 8°2'22.47"W |
| La Mascaronne, Fazioli, 2011 (Syrah with Cabernet Sauvignon grape) | Côte de Provence, France | 43°10'23.40"N, °18'47.64"W |
| Milk | | |
| Elmhurst Dairy (#36-2107) | Worcester Crys DBA Mountainside Farm, Roxbury, NY | 42°18'23.29"N, 74°32'59.09"W |
| Farmland Fresh Dairies (#42-169) | Dairy, Pottsville Pike, Reading, PA | 40°22'53.40"N, 75°56'06.20"W |
| Beer | | |
| Budweiser (#BG87) | Anheuser-Busch, St. Louis, MO | N/A |
| Heineken (#6167528F0923) | White Plains, NY | N/A |
| *Biofluid Biological Samples* | | |
| Saliva | | |
| male | New York, NY | N/A |
| female | New York, NY | N/A |
| Urine | | |
| male | New York, NY | N/A |
| female | New York, NY | N/A |
| Whole blood | | |
| male | New York, NY | N/A |
| female | New York, NY | N/A |
| Blood plasma | | |
| male | New York, NY | N/A |
| female | New York, NY | N/A |

Example 1—Detection Limits

The elements of all aqueous samples evaluated by the si-ICP-MS method and the isotopes monitored for determining element concentration values are given in Table 3.

Detection limits were determined by calculation of the y axis intercept of the calibration regression line, taking the calibration, blank standards and interferences into account. Due to daily instrument fluctuations, detection limits vary daily and are specific for each isotope independently. Exemplary detection limit ranges determined using the method of the present invention are shown in Table 5. The detection limits identified in Table 5 were generated by hand-pipetting standards, and manually administering standards and test samples to the ICP-MS. It is expected that the use of automated equipment (e.g., a pipetting robot and an autosampler) will improve these detection limit ranges substantially.

Lake Water (Lake Canandaigua, N.Y., USA, and Lake Baikal, Russia):

The most prominent difference between the lakes is the high concentration of Na, Mg, Si, K, Cr, Fe, Ni, Cu and Pb in the U.S. lake.

River Water (Delaware River, USA, and Nidda River, Germany):

The German river has higher concentrations of elements such as Li, K, Cr, Mn, Ni, Cu, Cs and U, yet Pb is not present, in contrast to the Delaware River. Rare Earth Elements are present in both samples in different and distinguishable patterns.

Sea Water (NJ Shore, USA, and Miami Beach, Barbados):

The sea water samples are the only samples with Rare Earth Element concentrations exceeding 1 µg/L. Both samples show high concentrations of U and Pb. Only the water off the New Jersey shore contains traceable amounts

TABLE 5

Detection limit ranges for each element

| Element | Detection Range [µg/L] | | Element | Detection Range [µg/L] | | Element | Detection Range [µg/L] | | Element | Detection Range [µg/L] | |
|---|---|---|---|---|---|---|---|---|---|---|---|
| Li | 4.15 | 5.65 | Co | 0.020 | 0.050 | Cd | 0.066 | 0.371 | Er | 0.061 | 0.344 |
| Be | 13 | 21 | Ni | 0.063 | 1.52 | In | 0.011 | 0.022 | Tm | 0.012 | 0.024 |
| B | 8.64 | 33 | Cu | 0.086 | 0.240 | Sn | 0.205 | 0.058 | Yb | 0.041 | 0.174 |
| Na | 2.42 | 25 | Zn | 0.094 | 0.899 | Sb | 0.061 | 0.267 | Lu | 0.038 | 0.047 |
| Mg | 2.75 | 54 | Ga | 0.041 | 0.099 | I | 0.152 | 1.20 | Hf | 0.025 | 0.165 |
| Al | 0.396 | 4.14 | Ge | 0.096 | 1.01 | Te | 0.007 | 0.213 | Ta | 0.109 | 0.009 |
| Si | 0.254 | — | As | 0.546 | 1.08 | Cs | 0.063 | 0.062 | W | 0.052 | 0.187 |
| P | 27 | 258 | Se | 0.599 | 5.09 | Ba | 0.043 | 0.554 | Re | 0.013 | 0.139 |
| S | 176 | 246 | Br | 1.10 | 3.23 | La | 0.003 | 0.044 | Os | 0.000 | 0.545 |
| Cl | 704 | 1600 | Rb | 0.115 | 0.126 | Ce | 0.046 | 0.043 | Ir | 0.038 | 0.160 |
| K | 0.194 | — | Sr | 0.063 | 0.047 | Pr | 0.020 | 0.017 | Pt | 0.125 | 0.354 |
| Ca | 495 | 1840 | Y | 0.025 | 0.023 | Nd | 0.028 | 0.299 | Au | 0.007 | 0.028 |
| Sc | 0.223 | — | Zr | 0.070 | 0.551 | Sm | 0.018 | 0.304 | Hg | 0.049 | 0.220 |
| Ti | 0.235 | — | Nb | 0.011 | 0.019 | Eu | 0.015 | 0.041 | Tl | 0.041 | 0.103 |
| V | 0.102 | | Mo | 0.256 | 0.139 | Gd | 0.030 | 0.179 | Pb | 0.050 | 0.218 |
| Cr | 0.088 | 2.90 | Ru | 0.019 | 0.340 | Tb | 0.020 | 0.055 | Bi | 0.015 | 0.014 |
| Mn | 0.049 | 0.041 | Pd | 0.117 | 0.288 | Dy | 0.010 | 0.125 | U | 0.103 | 0.092 |
| Fe | 0.704 | 2.50 | Ag | 0.019 | 0.108 | Ho | 0.025 | 0.013 | | | |

Example 2—Environmental Water Samples

Elemental concentrations in different water types (tap water, rain, etc.) are clearly distinguishable (see FIG. 1). Results show that different samples of one water type exhibit different elemental patterns. This "water fingerprinting" reflects the elemental contributions from the biosphere, which contains the hydrosphere, lithosphere, and atmosphere.

Tap water (Middleton, N.J. household):

In water drawn immediately upon turning on the tap after the water was in the pipe for at least 4 hours (Tap 0-min), elements such as P, Cs, W, Hg and Pb are more abundant. Elements such as Cu, Zn, Zr, Ag, Sn and Au are at higher concentrations in water drawn after 5 min running (Tap 5-min).

Well Water (2 and 3; Fresno, Calif.):

High concentration differences in well water can only be found in some elements, such as the transition metals Mn, Cu, Rb, Zr, Cd, and W. The element U is at high concentration (4.7 and 10.9 ppb).

Rain (Barbados, Beijing):

Rain from Beijing clearly differs from Barbados rain in that elements such as Na, Mg, V, Ni, Cu, Zn, Br, Zr and Cd are less abundant, in contrast to lead (Pb) concentration.

of the heavy metals Cd and Hg, and Sn and Sb are clearly present in higher concentrations.

Snow (Lassen Volcanic National Park and Crater Lake National Park, CA):

Elemental concentrations are lower compared to other environmental water samples, especially for Ni, Br, Rb, Sr, Mo, I and Ba. Between the snow samples, patterns of elemental concentrations vary: Cr, Cu, Zr and Sb are clearly higher concentrated in Crater Lake National Park snow, yet concentrations of Ru, Nd, Dy, Er and Yb are higher in Lassen Volcanic National Park snow.

Example 3—Beverage Samples

Figure 2:
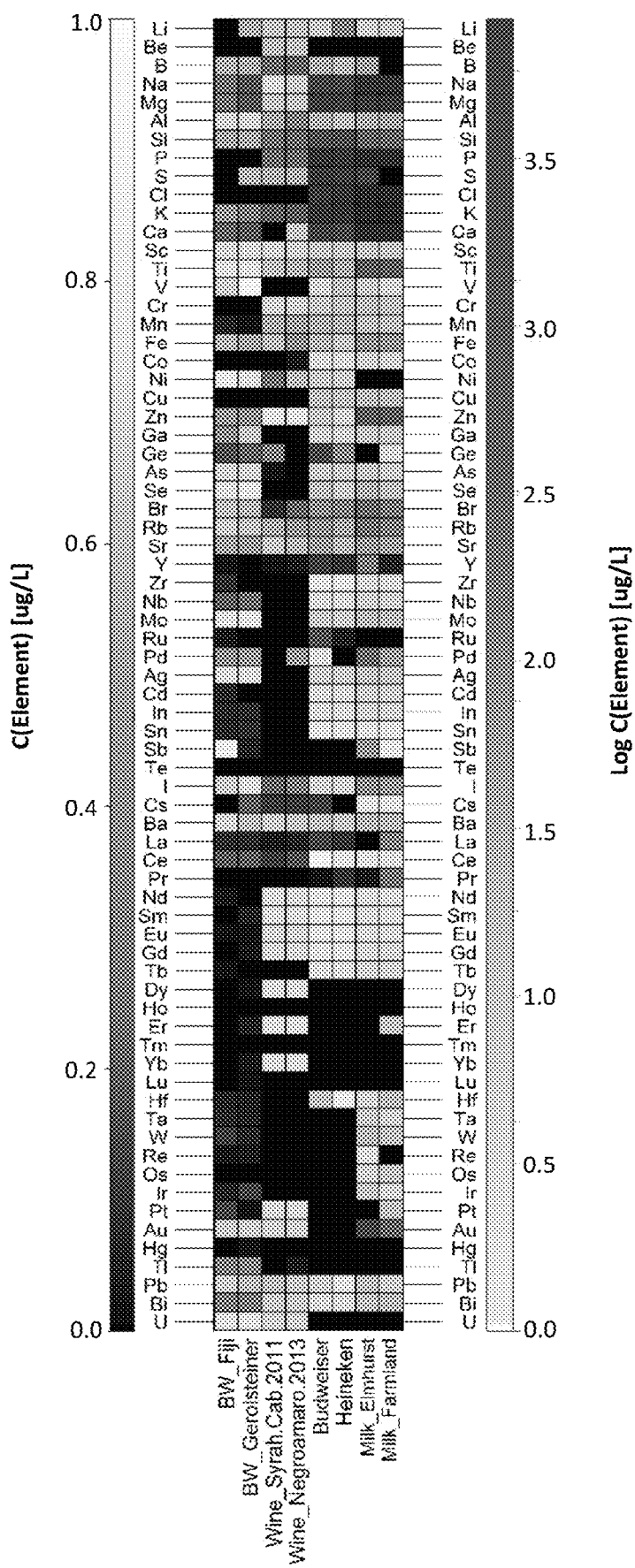
FIG. 2 shows the element concentration patterns in beverages. Trace concentrations between not detected (black) and 1 μg/L (white) are shown in shades of blue. Concentrations above 1 μg/L are represented by warm colors, in a logarithmic scale, and range from 1 μg/L (white) to over 1700 mg/L (dark red).

Elemental concentrations in different beverage samples, even beverage samples that are of the same class (bottled water, beer, and wine), are clearly distinguishable from one another (see FIG. 2). This confirms that the elemental contributions from the biosphere and, perhaps, environmental considerations associated with beverage processing and storage can be discerned.

Bottled Water (Fiji and Gerolsteiner):

Differences in elemental composition of bottled water is evidently present. Overall, Fiji contains higher trace concentrations of V, Zr, Ru, Cd, Nd, Eu, and Tb, while Gerolsteiner mineral water has much higher concentrations of Li, S, Ni, I, Ba, and U, and higher trace concentrations of Sm, Gd, Dy, Er, Yb, Lu, and Hg. Patterns of elemental concentrations throughout the periodic table are clearly distinguishable between the two bottled waters.

Wine (Schola Sarmenti and La Mascaronne):

The La Mascaronne from France contains a higher concentration of Pb and higher trace concentrations of Ge, and As, while the Schola Sarmenti from Italy has higher concentrations of Ca, Ti, Fe, and Sr, and higher trace concentrations of Pd and Ti. Both waters differ from the wine samples in elements of the 5th period: Zr, Nb, Mo, Tu, Pd, Ag, Cd, In, Sn, Sb, and Te, and have higher concentrations of Hf and Pb. While both samples show low concentrations of Rare Earth Elements they are, in general, similar in composition.

Beer (Budweiser and Heineken):

Budweiser shows much higher concentrations in Li, Pd, Cs and Ce, compared to Heineken. In contrast, Heineken exhibits much higher concentrations of Hf and Pb. While both beers show low concentrations of Rare Earth Elements, they are, in general, similar in composition.

Milk (Farmland Fresh Dairies and Elmhurst Dairy):

Besides high concentrations of Na, Mg, Ca, K and P, both milk samples show very high concentrations of Au, Ti, Pd and Zn. Rare Earth Elements such as Hf, Ta, W, Re, Os, Ir, Pt (Farmland Fresh Dairies), and Pb are all present in concentrations above 1 µg/L. The Elmhurst Dairy milk lacks Ge, La and Pt that are present in the Farmland Fresh Dairies milk, while Farmland Fresh Dairies has B, S and Re that Elmhurst Dairy does not have. Although similar in elemental patterns, both milk samples are clearly distinguishable based on elemental concentrations.

Example 4—Biofluid Biological Samples

Figure 3:
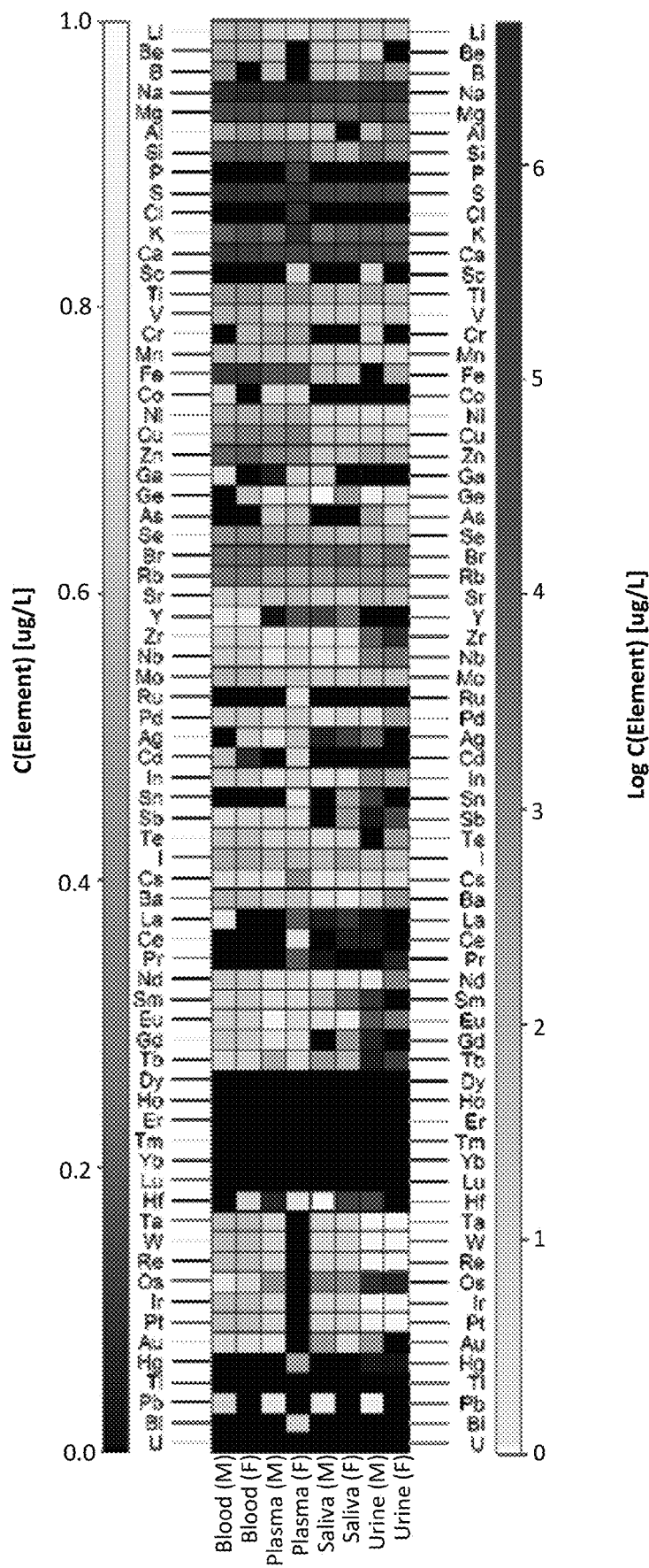
FIG. 3 shows the element concentration patterns in biofluids obtain from a male volunteer (M) and a female volunteer (F). Trace concentrations between not detected (black) and 1 μg/L (white) are shown in shades of blue. Concentrations above 1 μg/L are represented by warm colors, in a logarithmic scale, and range from 1 μg/L (white) to over 4500 mg/L (dark red).

Elemental concentrations in different biofluid samples are distinguishable between different samples from the same individual as well as between different individuals (FIG. 3). This illustrates differences in diet and environmental exposure.

Whole Blood and Plasma: Plasma and Whole Blood.

Plasma shows lower concentrations as the whole blood samples, especially in Rare Earth Elements such as Sm, Eu, Tb, Os, Nd, Gd, Ta, W, Re, Ir and Pt, but also Y and Zr (FIG. 3). The whole blood samples show individual concentration differences mainly in Pb, Hf, La, Cd, Ag, Ge, Ga, Co, Cr and B.

Saliva:

Elemental concentrations are in general lower in saliva compare to blood samples, mostly in rare earth elements, e.g., Sm Gd, Ta, W, and Pt (FIG. 3). Individual differences in elemental concentration patterns are visible: in T, Au and Pb were higher, and trace element concentrations were higher for Ge, Sn, Sb, Ce, and Hf, while the concentrations of M saliva was higher for Al and Ga, with trace concentrations higher for Pr.

Urine:

Urine samples show similar concentrations to saliva in some elements, e.g., Ag, Cd, Sn, Sb, La, Ce, Pr, Gd and Tb, and lower concentration in other elements such as Mn, Y, Zr, Nb, In, Te, Nd, Ta, W, Re, Os, Ir and Pt. The Urine of T compared to M was higher in concentration values for Be, Si, Sc, Cr, Pd, Ba, and Pb, with higher trace concentrations for Ag, Sn, La, Ce, Sm, Gd, and Hf. The urine of M had higher Al, and Fe, and higher trace concentrations of Te and Pr.

Discussion of Examples 1-4

The preceding Examples illustrate the potential for using the si-ICP-MS calibration method to quantify all elements present in an aqueous sample from $^6$Li to $^{238}$U simultaneously and in as little as 1 mL (when manually introduced into the instrument) of aqueous sample.

Choice of Internal Standards

In EPA Method 200.8 (Long and Martin, 1989), it is suggested to use five internal standards to cover the mass range from $^6$Li to $^{238}$U. Proposed elements are: Sc, Y, In, Tb, and Bi. Applicants used only three standards, $^6$Li, $^{103}$Rh, and $^{232}$Th, since each element used as an internal standard cannot be measured in the test samples, therefore reducing the number of measureable elements. Applicants also decided to deviate from the suggested elements and use a high concentrated $^6$Li internal standard, even though lithium is a bi-isotope element (Li$^6$ 7.5% and $^7$Li 92.5%), to cover the lower mass ranges. Experimental data shows that $^6$Li concentrations in water samples with high lithium concentrations (about 10 µg/L) do not interfere with the 10 mg/L $^6$Li internal standard. Although it is not known whether Rh and Th are naturally occurring in water samples, it can be expected that their concentrations are very low and the influence of potential sample concentrations are negligible compared to the artificially added internal standard. Even if the samples would contain Rh and/or Th, the additional amounts would be measureable and could be accounted for in the process of data analysis, e.g., Rh has been widely used in bodily fluid analysis (Goullé et al., 2005).

Choice of Calibration Standards

Although ICAL, Mix1 and Mix3, as well as Hg, In and Ca, and the Multi standard are stable and stored in similarly concentrated HNO$_3$ solutions, by extensive testing and analyses it was discovered that a combination of all standards results in inaccurate concentration measurements. This applies also for Cl and Br, as well as Mix2 and Os. In carrying out the preceding Examples it was discovered that inaccuracies are a direct result of three quirks of inorganic chemistry. They are:

1) Conflation of too many isotopes: Increasing the number of elements disproportionately increases the number of isotopes, which leads to polyatomic complexes masking as elements at some specific mass to charge ratio, artificially inflating the detection at one mass by multiple elements. Hence, the separating of isotope concentrations on the same mass becomes problematic.

2) Elemental stability: Element stability must also be considered when mixing many together. It was found that some combinations of mixes and single element standards resulted in precipitation, preventing an accurate measurement. When such samples enter the plasma, the sample becomes dissolved, atomized and ionized (Goullé et al., 2005; Pröfrock and Prange, 2012; Thomas, 2013). Ideally, elements are broken down into their respective positively charged isotope ions.

3) Interferences: Interferences are signals occurring in the measurement spectrum due to altered physical properties of ions, causing inaccuracies in the measurements. These interferences can be isobaric interferences, isobaric polyatomic interferences, abundance sensitivity, physical interferences, and memory interferences (Henshaw et al., 1989; Long and Martin, 1989; Leonhard et al., 2002; Pröfrock and Prange, 2012; Thomas, 2013). The more elements are involved within one calibration standard, the more complex it becomes to calibrate each one correctly. For example, in isobaric polyatomic interferences, ions of different elements collide and form a new ion. This new molecule has the combined mass of both isotopes and is detected at its respective mass. For example, if the most common oxygen isotope, $^{16}O$, fuses with the most common argon isotope, $^{40}Ar$. The new argon-oxide (ArO$^+$) molecule has a mass of 56 and would be detected together with the most common iron isotope, $^{56}Fe$ (Long and Martin, 1989; Leonhard et al., 2002; Pröfrock and Prange, 2012; D'Ilio et al., 2006). This would make it difficult to determine the correct amount of $^{56}Fe$. As with $^{56}Fe$, as many isotopes with such heavy interferences as possible were excluded.

Potentially, isotopes can collide with one another. The major origin of oxide formation is $^{16}O$, especially in water samples (deBoer et al., 1996). Therefore, reducing the number of elements within one standard solution can reduce the risk of interferences and incorrectly interpreted concentration values. The possibility of isotopes fusing, of course, depends on their natural abundance and ionization energy: highly abundant isotopes such as $^{24}Mg$ are more likely to fuse than less abundant isotopes, such as $^{25}Mg$. Yet, although $^{37}Cl$ is less abundant than $^{24}Mg$, it has a much higher ionization energy and therefore is more likely to fuse. In addition, some elements destabilize in combination with other elements. Possible interferences must be accounted for during optimization (deBoer et al., 1996; D'Ilio et al., 2006; Pröfrock and Prange, 2012; Ardelt et al., 2013) and when generating the calibration regression.

Elemental Limitations

One limitation of the si-ICP-MS calibration method is the sheer physical properties of this instrument, which prohibit detection of elements with mass to charge ratios of less than 5 and more than 243. This excludes hydrogen ($^1H$, $^2H$) and helium ($^4He$), as well as elements higher in mass than americium ($^{241}Am$, $^{243}Am$) from being detected.

In general Nobel Gases cannot be detected by the instrument, due to their high electronegativities and ionization energies. Electronegativity decreases with the periodic number and increases with group number throughout the periodic table, and is highest in F. Therefore, fluorine (F) cannot be analyzed with the disclosed method. In addition, argon is the carrier gas and Ar gas bottles contain random amounts of krypton (Kr) gas.

Carbon, nitrogen and oxygen are common contaminates in argon gas, which also prohibits these elements from being analyzed. Furthermore, samples are easily contaminated with these omnipresent elements during sampling, preparation and analysis.

Radioactive elements such as Tc, Pm, Po, At, Rn, Fr, Ra, Ac, Pa, Np, Pu and Am are not measured, as their standards are commercially available only with special permits.

Analytical Limitations.

Instrument specification sets detection limits (DL) for most elements at <0.01 µg/L, for Br at 0.2 µg/L, and for Cl at 10 µg/L. DL are lower for As and Hg (0.01 µg/L), Al, Mg, Sn, Pt and OS (0.005 µg/L) and all Rear Earth Elements, Transition Metals and U (~0.001 µg/L) (SPECTRO.com). Detection limits are calculated taking the calibration standards, the blank as well as interferences on each isotope into account and, hence, can slightly vary by day/run. Therefore, and, because DL are isotope and not element specific, detection limits are reported as ranges in Table 5.

Interferences can affect and influence the results of almost every measured isotope. The SPECTRO MS software can account for interferences that are caused by elements that have been calibrated for. Because the disclosed reagents and method do not calibrate and measure H, C, N and O, interferences caused be these elements remain unaccounted for. It was therefore assumed that interferences caused by H, C, N and O are similar within similar sample matrixes (e.g. within all water, or within all wine samples). This is reasonable assumption, because the calibration standard matrices were made to mimic the sample matrix (e.g., by adding EtOH into the calibration standards when measuring wine samples). It is no possible to control for interferences caused by elements of the internal standard: $^6Li$ together with hydrogen interferes on $^7Li$, to some degree. Potentially effected isotopes by $^{103}Rh$ (together with C, O, H and Ar) are $^{51}V$, $^{52}Cr$, $^{115}In$, $^{120}Sn$, and $^{143}N$, although no such interferences were detected in carrying out the work reported in the preceding Examples.

For environmental water samples, bottled water, wine and beer, as well as saliva and urine (assumed to have a water content of >95%, especially when diluted), the objective of achieving matrix similarities in the calibration standards, the blank, the samples and the controls was met. However, this objective was not met when analyzing milk and blood samples. Despite this, the ability of performing the analyses with a wide range of applications was demonstrated. When pursuing blood and milk analysis, it is recommended to match the matrices of calibration standards, blank and controls with the respective samples, and furthermore to adjust SRM accordingly (Herwig et al., 2011; Martino et al., 2001; Ataro et al., 2008; Reid et al., 2008).

Although extensive testing of calibration standard concentrations, it occasionally happens that samples contain elements in higher concentration than calibrated for. The software then provides a minimum concentration of the respective isotope or element.

"Simultaneous" ICP-MS

No existing quadrupole-based se-ICP-MS provides simultaneous detection and recording of multiple elements, let alone of the mass spectrum from $^6Li$ to $^{238}U$. There is thus some confusion in the literature regarding the use of the term "simultaneous". Many articles use this term in their titles, yet they employ a conventional quadrupole mass spectrometer in their experimental design (Rahil-Khazen et al., 2000; Taylor et al., 2003; D'Ilio et al., 2006; Bressy et al., 2013; Khan et al., 2013; Loope et al., 2013; Yeghicheyan et al., 2013; Peng et al, 2015). What these investigators mean by the term "simultaneous" is storage and readout of multi-element data from the mass spectrometer using a multichannel analyzer. Multi-element detection is still classical se-ICP-MS, measuring one element at a time. For this reason, quantitative multi-element measurements on se-ICP-MS instruments are somewhat constrained in the breadth of the inorganic spectrum that can be measured with any one multi-element calibration standard (Stetzenbach et al., 1994; DeBoer et al., 1996; Fernandez-Turiel et al. 2000; Forrer et al., 2001; Leonhard et al., 2002; Goullé et al., 2005; Heitland and Köster, 2006; Gonzálvez et al., 2008; Kracher and Shotyk, 2009; Louie et al. 2012; Pröfrock and Prange, 2012; Jabłońska-Czapla et al., 2014; Khan et al., 2014; Šelih et al., 2014; Statt et al., 2014; Mohd-Taufek et al., 2016). This technology is in contrast to the si-ICP-MS technology and the method described herein, in which a number of grouped standards, for example 11 or 12, are iteratively dispensed to calibrate the instrument upon which simultaneous detection and measurement from $^6$Li to $^{238}$U is possible.

Samples

In respect of the aqueous samples chosen as exemplars in this study, patterns of elemental concentrations throughout the periodic table are clearly distinguishable between the various categories of water, beverage and biofluid.

Tap waters distinguish unique chemical profiles characterizing local plumbing infrastructure and treated environmental source water. Among waters from Central Valley, Calif. wells, the high concentration of U reflects the geochemical environment, exacerbated by pumping and irrigation practices, particularly as they are affected by drought (Jurgens et al., 2010). The concentrations of several elements in Beijing rainwater are in general agreement with a previous study (Yang et al., 2012), but Pb was not investigated in that study. Example 2 demonstrates a high concentration of Pb in Beijing rainwater, which is not surprising, because the air quality of this city is among the poorest in the world. Lake and river waters likely reflect the complex geochemistry of their region. Sea water is exceptional in comparison to the fresh waters tested, in having a large proportion of heavy elements. The concentrations of most light elements is high in snow, and in only trace concentrations for the heavy elements.

Overall, lowest concentrations are found in the snow samples (especially in Br, Rb, Sr, Mo, I and Ba), whereas overall highest concentrations are found in the sea water samples (especially in elements from the 5th period and up (Zr to U). All samples, but the sea water samples, show high concentrations of Na, Mg and Ca, and low concentrations of elements heavier than Y, with the exceptions of Mo, I, Ba and sometimes U.

Concentrations among the beverages tested reveal surprising variability. The levels of Li in Gerolsteiner bottled water may be at concentrations sufficient to affect mood. High concentration values for S in wine is likely due to sulfur dioxide added as a preservative to protect it from oxidizing. Levels of Pb in the wine tested are much higher than would occur in a natural fruit, and its origin is debated, but it may derive from Pb in brass tubes and faucets used in wineries (Kauffmann, 1998). The beer samples are very similar, and most similar to the bottled waters tested, except that there is no detectable U. The beer samples also contain higher concentrations of Pr and Si, perhaps derived from the glass bottles. Milk samples are distinguished from the other beverages by very high concentrations of Ti, Zn, Pd, and Au.

Of the biofluid samples, overall concentrations decrease from whole blood samples to plasma samples and saliva samples, and are lowest in urine. Rare earth elements such as Dy, Ho, Er, Tm, Yb, Lu, Tl, Bi and U are not present in any of the samples tested. Of the biofluid samples, Hg was only found in urine samples. The male test person is under a physician's care for peripheral neuropathy, which has been traced to high levels of Pb in toxicological analysis of the blood sample, which was also detected in his plasma and urine samples. The higher level of Au in the saliva of the male test person may be due to a gold restoration on one of his teeth.

Applicability of the Water Fingerprinting Method

The si-ICP-MS calibration method is a "Water Fingerprinting Method", which is applicable to all aqueous samples and can be used to advance personal health, in general, and public health, in particular, as the monitoring of 71 elements in water we consume and biofluids is easy, quick, and cost efficient. The method can be used to understand common concentration level ranges of each relevant element between $^6$Li and $^{238}$U in humans, exceeding by far the number of commonly monitored elements. The mapping of elemental patterns in human bodily fluids might also be beneficial for the understanding of diseases, their origin, emergences or manner of transmission. In combination with (tap) water analysis, the method may find its application in forensics: unique total elemental water patterns might be matched to unique total elemental blood, plasma, saliva or urine patterns. The digestion of hair and tissue samples or the extension of this method to solids by laser ablation-inductively coupled plasma-mass spectrometry, will further aid the identification of specific elemental concentration patterns in human tissues.

The elemental mapping of concentration levels in bottled water and tap water will help to increase our understanding of "normal" concentration levels of relevant elements in water. Many elements are known to affect human health negatively, yet only 19 elements are monitored by the EPA. For example, lithium is known to be embryo toxic, yet there is no maximum concentration limit for lithium in drinking water.

Besides the method's effect on (public) health issues, it will also find an application in "forensic" tracing of the origins of (bottled) water, wine, milk, beer and other foods. Knowing the elemental composition of beverages and foods will increase our understanding of elemental distributions among consumed items (especially macro- and micronutrients) and be used to determine their origin.

Given that each water sample, may it come from rain, snow, fog, aquifer, puddle, river, stream, lake, or sea, has its own unique elemental concentration pattern, the Water Fingerprinting Method enables further research to map the world according to its elemental distributions and compositions, hence revealing elemental flows through the environment.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims. Accordingly, the invention is limited only by the following claims and equivalents thereto.

REFERENCES

All references cited throughout the present application are hereby incorporated by reference in their entirety. The citations of those references are provided below.

Henshaw, J. M., E. M. Heithmar, and T. A. Hinners, *Inductively coupled plasma mass spectrometric determination of trace elements in surface waters subject to acidic deposition.* Analytical Chemistry, 1989. 61: p. 335-342.

Fernandez-Turiel, J. L., et al., *Strategy for water analysis using ICP-MS.* Fresenius' Journal of Analytical Chemistry, 2000. 368: p. 601-606.

Ding, C. G., et al., *Inductively coupled plasma mass spectrometry for the simultaneous determination of thirty metals and metalloids elements in blood samples.* Zhonghua yu fang yi xue za zhi [Chinese Journal of Preventive Medicine], 2012. 46: p. 745-749.

Gonzálvez, A., et al., *Searching the most appropriate sample pretreatment for the elemental analysis of wines by inductively coupled plasma-based techniques*. Journal of Agricultural and Food Chemistry, 2008. 56: p. 4943-4954.

Jabłońska-Czapla, M., et al., *Development and validation of HPLC-ICP-MS method for the determination inorganic Cr, As and Sb speciation forms and its application for Plawniow ice reservoir (Poland) water and bottom sediments variability study*. Talanta, 2014. 120: p. 475-483.

Khan, N., et al., *Method validation for simultaneous determination of chromium, molybdenum and selenium in infant formulas by ICP-OES and ICP-MS*. Food Chemistry, 2013. 141: p. 3566-3570.

Krachler, M. and W. Shotyk, *Trace and ultratrace metals in bottled waters: survey of sources worldwide and comparison with refillable metal bottles*. Science of the Total Environment, 2009. 407: p. 1089-1096.

Kubová, J., V. Nevoral, and V. Streško, *Determination of rare earth elements in mineral waters by inductively coupled plasma atomic emission spectrometry*. Journal of Analytical Atomic Spectrometry, 1994. 9: p. 241-243.

Leonhard, P., et al., *Analysis of diluted sea-water at the ng L-1 level using an ICP-MS with an octopole reaction cell*. Journal of Analytical Atomic Spectrometry, 2002. 17: p. 189-196.

Loope, G. R., L. R. Kump, and M. A. Arthur, *Shallow water redox conditions from the Permian-Triassic boundary microbialite: The rare earth element and iodine geochemistry of carbonates from Turkey and South China*. Chemical Geology, 2013. 351: p. 195-208.

Pröfrock, D. and A. Prange, *Inductively Coupled Plasma-Mass Spectrometry (ICP-MS) for quantitative analysis in environmental and life sciences: a review of challenges, solutions, and trends*. Applied Spectroscopy, 2012. 66: p. 843-868.

Rahil-Khazen, R., et al., *Validation of inductively coupled plasma atomic emission spectrometry technique (ICP-AES) for multi-element analysis of trace elements in human serum*. Scandinavian Journal of Clinical and Laboratory Investigation, 2000. 60: p. 677-686.

Šelih V. S., et al., *Multi-element analysis of wines by ICP-MS and ICP-OES and their classification according to geographical origin in Slovenia*. Food Chemistry, 2014. 153: p. 414-423.

Taylor, V. F., H. P. Longerich, and J. D. Greenough, *Multi-element analysis of Canadian wines by inductively coupled plasma mass spectrometry (ICP-MS) and multivariate statistics*. Journal of Agricultural and Food Chemistry, 2003. 51: p. 856-860.

Yeghicheyan, D., et al., *A Compilation of Silicon, Rare Earth Element and Twenty-One other Trace Element Concentrations in the Natural River Water Reference Material SIRS-5 (NRC-CNRC)*. Geostandards and Geoanalytical Research, 2013. 37: p. 449-467.

Ammann, A. A., *Speciation of heavy metals in environmental water by ion chromatography coupled to ICP-MS*. Analytical and Bioanalytical Chemistry, 2002. 372: p. 448-452.

Ardelt, D., et al., *Isotope ratio measurements with a fully simultaneous Mattauch-Herzog ICP-MS*. Analytical and Bioanalytical Chemistry, 2013. 405: p. 2987-2994.

D'Ilio, S., et al., *Simultaneous quantification of 17 trace elements in blood by dynamic reaction cell inductively coupled plasma mass spectrometry (DRC-ICP-MS) equipped with a high-efficiency sample introduction system*. Analytica Chimica Acta, 2006. 579: p. 202-208.

De Boer, J. L. M., et al., *Levels of rare earth elements in Dutch drinking water and its sources. Determination by inductively coupled plasma mass spectrometry and toxicological implications. A pilot study*. Water Research, 1996. 30: p. 190-198.

Forrer, R., K. Gautschi, and H. utz, *Simultaneous measurement of the trace elements Al, As, B, Be, Cd, Co, Cu, Fe, Li, Mn, Mo, Ni, Rb, Se, Sr, and Zn in human serum and their reference ranges by ICP-MS*. Biological Trace Element Research, 2001. 80: p. 77-93.

Goullé, J. P., et al., *Metal and metalloid multi-elementary ICP-MS validation in whole blood, plasma, urine and hair: Reference values*. Forensic Science International, 2005. 153: p. 39-44.

Heitland, P. and H. D. Köster, *Biomonitoring of 37 trace elements in blood samples from inhabitants of northern Germany by ICP-MS*. Journal of Trace Elements in Medicine and Biology, 2006. 20: p. 253-262.

Kantipuly, C. J. and A. D. Westland, *Review of methods for the determination of lanthanides in geological samples*. Talanta, 1988. 35: p. 1-13.

Long, S. E. and T. D. Martin, *Method 200.8, Determination of trace elements in waters and wastes by inductively coupled plasma-mass spectrometry*, E.M.S. Laboratory, Editor 1989, United States Environmental Protection Agency: Cincinnati, Ohio. p. 1-57.

Lyon, T. D., et al., *Evaluation of inductively coupled argon plasma mass spectrometry (ICP-MS) for simultaneous multi-element trace analysis in clinical chemistry*. Journal of Analytical Atomic Spectrometry, 1988. 3: p. 265-271.

Mohd-Taufek, N., et al., *The simultaneous analysis of eight essential trace elements in human milk by ICP-MS*. Food Analytical Methods, 2016. 9: p. 2068-2075.

Staff, J. F., et al., *Investigation of saliva as an alternative matrix to blood for the biological monitoring of inorganic lead*. Toxicology Letters, 2014. 231: p. 270-276.

Stetzenbach, K. J., et al., *Testing the limits of ICP-MS: determination of trace elements in ground water at the part-per-trillion level*. Ground Water, 1994. 32: p. 976-985.

Zhang, S. J., X. Y. Zhuo, and D. Ma, [*Developments in determination of elements using ICP-MS in blood and urine*]. Fa yi xue za zhi, 2012. 28: p. 456-60.

Louie, H., et al., *A study of techniques for the preservation of mercury and other trace elements in water for analysis by inductively coupled plasma mass spectrometry (ICP-MS)*. Analytical Methods, 2012. 4: p. 522-529.

WHO, *Guidelines for drinking-water quality*. Fourth Edition ed, ed. W. H. Organization2011, Geneva, Switzerland: World Health Organization. 564.

Khan, N., et al., *Analysis of minor and trace elements in milk and yogurts by inductively coupled plasma-mass spectrometry (ICP-MS)*. Food Chemistry, 2014. 147: p. 220-224.

Barbosa Jr, F., et al., *Evaluation of the use of salivary lead levels as a surrogate of blood lead or plasma lead levels in lead exposed subjects*. Archives of Toxicology, 2006. 80: p. 633-637.

Koh, D., et al., *Can salivary lead be used for biological monitoring of lead exposed individuals?* Occupational and Environmental Medicine, 2003. 60: p. 696-698.

Nriagu, J., et al., *Lead levels in blood and saliva in a low-income population of Detroit, Mich*. International Journal of Hygiene and Environmental Health, 2006. 209: p. 109-121.

Bressy, F. C., et al., *Determination of trace element concentrations in tomato samples at different stages of maturation by ICP OES and ICP-MS following microwave-assisted digestion*. Microchemical Journal, 2013. 109: p. 145-149.

Garbe-Schönberg, C. D., *Simultaneous determination of thirty-seven elements in twenty-eight international rock standards by ICP-MS*. Geostandards Newsletter, 1993. 17: p. 81-97.

Ardelt, D., U. Heynen, and A. A. Scheidemann, U.S.P.a.T. Office, Editor 2016: Washington, D.C.

EU, *Council Directive 98/83/EC on the quality of water intented for human consumption*, C.o.t.E. Union, Editor 1998, Official Journal of the European Communities: Brussels, Belgium. p. 330-354.

EPA, *Drinking Water Standards and Health Advisories*, O.o. Water, Editor 2012 U.S. Environmental Protection Agency: Washington, D.C. p. 1-12.

Thomas, R., *Practical guide to ICP-MS: A Tutorial For Beginners*. Third Edition ed2013, Boca Raton, Fla.: CRC press Peng, H., et al., *Simultaneous speciation analysis of inorganic arsenic, chromium and selenium in environmental waters by 3-(2-aminoethylamino) propyltrimethoxysilane modified multi-wall carbon nanotubes packed microcolumn solid phase extraction and ICP-MS*. Talanta, 2015. 131: p. 266-272.

Jurgens, B. C., et al., *Effects of groundwater development on uranium: Central Valley, Calif., USA*. Ground Water, 2010. 48: p. 913-928.

Yang, F., et al., *Five-year record of atmospheric precipitation chemistry in urban Beijing, China*. Atmospheric Chemistry and Physics 2012. 12: p. 2025-2035.

Kauffmann, A., *Lead in wine*. Food Additives and Contaminants 1998. 15: p. 437-445.

Feldman, C., *Preservation of dilute mercury solutions*. Analytical Chemistry, 1974. 46: p. 99-102.

Herwig, N., et al. *Multi-element screening in milk and feed by SF-ICP-MS*. Food Chemistry, 2011, 124(3), 1223-1230.

Martino, F. A. R., et al., *The potential of double focusing-ICP-MS for studying elemental distribution patterns in whole milk, skimmed milk and milk whey of different milks*. Analytica chimica acta, 2001, 442(2), 191-200.

Ataro, A., et al., *Quantification of trace elements in raw cow's milk by inductively coupled plasma mass spectrometry (ICP-MS)*. Food Chemistry, 2008, 111(1), 243-248.

Reid, H. J., et al., *Determination of iodine and molybdenum in milk by quadrupole ICP-MS*. Talanta, 2008, 75(1), 189-197.

Dame, Z. T., et al., *The human saliva metabolome*. Metabolomics, 2015, 11(6), 1864-1883.

Vaughan, M. A., et al., *Multielement analysis of biological samples by inductively coupled plasma-mass spectrometry. II. Rapid survey method for profiling trace elements in body fluids*. Clinical Chemistry, 1991, 37(2), 210-215.

Kim, Y. J., et al., *Effects of smoking on trace metal levels in saliva*. Oral Diseases, 2010, 16(8), 823-830.

What is claimed:

1. A method for simultaneously detecting absolute concentrations of a plurality of elements in a liquid sample, the method comprising:
   a) providing an internal standard comprising a combination of three elements selected from different periods on the periodic table of elements, the three selected elements being present in the internal standard at known concentrations;
   b) providing a plurality of calibration standards, the plurality of calibration standards collectively comprising known concentrations of at least two of Li, Be, B, Na, Mg, Al, Si, P, S, Cl, K, Ca, Sc, Ti, V, Cr, Mn, Fe, Co, Ni, Cu, Zn, Ga, Ge, As, Se, Br, Rb, Sr, Y, Zr, Nb, Mo, Ru, Rh, Pd, Ag, Cd, In, Sn, Sb, Te, I, Cs, Ba, La, Ce, Pr, Nd, Sm, Eu, Gd, Tb, Dy, Ho, Er, Tm, Yb, Lu, Hf, Ta, W, Re, Os, Ir, Pt, Au, Hg, Tl, Pb, Bi, Th, and U, each of the calibration standards being provided in at least two different concentrations;
   c) introducing a known concentration of the internal standards into each of the plurality of calibration standards, a blank standard, and a liquid sample to be tested; and
   d) introducing each of the plurality of calibration standards, the blank standard, and the liquid sample to be tested individually into an inductively coupled plasma mass spectrometer to simultaneously detect one or more ionization products of elements present in each of the plurality of calibration standards, the blank standard, and the liquid sample to be tested; and
   e) determining an absolute concentration of the one or more detected elements in the liquid sample relative to the one or more detected ionization products of elements in the plurality of calibration standards.

2. The method according to claim 1, wherein the inductively coupled plasma mass spectrometer has a multichannel monolithic complementary metal oxide semiconductor (CMOS) strip detector array configured to simultaneously perform detection over a range of multiple masses.

3. The method according to claim 1, wherein the internal standard comprises $^6$Li, $^{103}$Rh, and $^{232}$Th, or $^{89}$Y and $^{159}$Tb instead of $^{103}$Rh and 232Th.

4. The method according to claim 3, wherein $^6$Li is present in each internal standard at a concentration range of about 2 to 50 mg/L combined with either $^{103}$Rh and $^{232}$Th, or $^{103}$Rh and $^{159}$Tb, or $^{89}$Y and $^{232}$Th, or $^{89}$Y and $^{159}$Tb, at a concentration of range of about 0.5 to about 50 mg/L.

5. The method according to claim 3, wherein $^6$Li is present in the internal standard at a concentration of about 10 mg/L, $^{89}$Y or $^{103}$Rh are present in the internal standard at a concentration of about 2 mg/L, and $^{159}$Tb or $^{232}$Th are present in the internal standard at a concentration of about 2 mg/L.

6. The method according to claim 1, wherein the plurality of calibration standards collectively comprise known concentrations of each of Li, Be, B, Na, Mg, Al, Si, P, S, Cl, K, Ca, Sc, Ti, V, Cr, Mn, Fe, Co, Ni, Cu, Zn, Ga, Ge, As, Se, Br, Rb, Sr, Y, Zr, Nb, Mo, Ru, Rh, Pd, Ag, Cd, In, Sn, Sb, Te, I, Cs, Ba, La, Ce, Pr, Nd, Sm, Eu, Gd, Tb, Dy, Ho, Er, Tm, Yb, Lu, Hf, Ta, W, Re, Os, Ir, Pt, Au, Hg, Tl, Pb, Bi, Th, and U.

7. The method according to claim 6, wherein known concentrations of elements in the plurality of provided calibration standards varies between about 0.1 part per billion (ppb) and about 1000 parts per million (ppm).

8. The method according to claim 1, wherein the absolute concentration of the one or more detected elements in the liquid sample does not include an absolute concentration of the three elements present in the internal standard.

9. The method according to claim 1, wherein the liquid sample is a water sample, a biological fluid sample, a beverage sample, or an aqueous solution containing 1% or less total dissolved solids.

10. The method according to claim 1, wherein the blank sample comprises purified water and $HNO_3$ prior to said introducing a known volume of the internal standard.

11. The method according to claim 1, further comprising:
f) comparing the determined, absolute concentration of the one or more detected elements in the liquid sample to a guideline standard.

12. The method according to claim 1, further comprising:
f) comparing the determined, absolute concentration of the one or more detected elements in the liquid sample to an absolute concentration of the one or more detected elements in a reference product of established provenance; and
g) determining whether the liquid sample is comparable to the reference product of established provenance.

13. The method according to claim 1, comprising:
carrying out the recited steps c) to e) on a first water sample obtained from a water source; and repeating the recited steps c) to e) on a second water sample obtained from the water source at a later point in time.

14. An internal standard composition for mass spectrometry comprising a combination of three elements selected from different periods on the periodic table of elements, wherein each of the three elements is present at a concentration within a range of about 0.05 to about 100 mg/L.

15. The internal standard composition according to claim 14, wherein one of the three elements is selected from period 2, one of the three elements is selected from period 4 or period 5, and one of the three elements is selected from period 6 or period 7.

16. The internal standard composition according to claim 14, wherein the three elements are $^6$Li, $^{103}$Rh, and $^{232}$Th; or $^6$Li, $^{103}$Rh, and $^{159}$Tb, or $^6$Li, $^{89}$Y, and $^{232}$Th; or $^6$Li, $^{89}$Y and $^{159}$Tb.

17. The internal standard composition according claim 16, wherein $^6$Li is present at a concentration of about 10 mg/L, $^{89}$Y or $^{103}$Rh is present at a concentration of about 2 mg/L, and $^{159}$Tb or $^{232}$Th is present at a concentration of about 2 mg/L.

18. A blank standard composition for mass spectrometry comprising ultrapure water, $HNO_3$, and the internal standard composition according to claim 14.

19. The blank standard composition according to claim 18, wherein the ultrapure water comprises about 97.5% v/v, about 1.5% $HNO_3$ v/v, and about 1% v/v of the internal standard composition.

20. The blank standard composition according to claim 19, wherein the blank standard composition comprises $^6$Li at a concentration of about 100 µg/L, $^{89}$Y or $^{103}$Rh is present at a concentration of about 20 µg/L, and $^{159}$Tb or $^{232}$Th is present at a concentration of about 20 µg/L.

21. A kit comprising:
an internal standard comprising a combination of three elements selected from different periods on the periodic table of elements, the three selected elements being present in the internal standard at known concentrations; and
a plurality of calibration standards, the plurality of calibration standards collectively comprising known concentrations of Li, Be, B, Na, Mg, Al, Si, P, S, Cl, K, Ca, Sc, Ti, V, Cr, Mn, Fe, Co, Ni, Cu, Zn, Ga, Ge, As, Se, Br, Rb, Sr, Y, Zr, Nb, Mo, Ru, Rh, Pd, Ag, Cd, In, Sn, Sb, Te, I, Cs, Ba, La, Ce, Pr, Nd, Sm, Eu, Gd, Tb, Dy, Ho, Er, Tm, Yb, Lu, Hf, Ta, W, Re, Os, Ir, Pt, Au, Hg, Tl, Pb, Bi, Th, and U, each of the calibration standards being provided in at least two different concentrations.

22. The kit according to claim 21, wherein the three elements are $^6$Li, $^{89}$Y or $^{103}$Rh, and $^{159}$Tb or $^{232}$Th, and each of the three elements is present at a concentration within a range of about 0.05 to about 100 mg/L.

23. The kit according to claim 21, wherein the plurality of calibration standards comprise at least three different calibration standards.

* * * * *